United States Patent
Sarwal et al.

(10) Patent No.: US 6,662,052 B1
(45) Date of Patent: Dec. 9, 2003

(54) METHOD AND SYSTEM FOR NEUROMODULATION THERAPY USING EXTERNAL STIMULATOR WITH WIRELESS COMMUNICATION CAPABILITES

(75) Inventors: Alok Sarwal, Highlands Ranch, CO (US); Birinder R. Boveja, Greenfield, WI (US)

(73) Assignee: NAC Technologies Inc.

( * ) Notice: Subject to any disclaimer, the term of this patent is extended or adjusted under 35 U.S.C. 154(b) by 61 days.

(21) Appl. No.: 09/837,565

(22) Filed: Apr. 19, 2001

(51) Int. Cl.[7] .................................................. A61N 1/08
(52) U.S. Cl. ............................ 607/59; 607/59; 607/60; 607/61
(58) Field of Search ..................... 607/1–2, 7, 10–12, 607/15, 17, 30–60, 65–76, 115–118, 123, 142, 148–156; 600/382–394, 300, 486

(56) References Cited

U.S. PATENT DOCUMENTS

| 4,702,254 A | 10/1987 | Zabara et al. ................ 128/421 |
| 4,771,779 A | 9/1988 | Tanagho et al. ........ 128/419 E |
| 4,867,164 A | 9/1989 | Zabara et al. ................ 128/421 |
| 5,025,807 A | 6/1991 | Zabara et al. ................ 128/421 |
| 5,215,086 A | 6/1993 | Terry, Jr. et al. ............. 128/421 |
| 5,458,122 A | 10/1995 | Hethuin ....................... 128/696 |
| 5,759,199 A | 6/1998 | Snell et al. .................... 607/60 |
| 5,978,713 A | 11/1999 | Prutchi ......................... 607/60 |
| 5,997,476 A | 12/1999 | Brown ......................... 600/300 |
| 6,208,902 B1 * | 3/2001 | Boveja ......................... 607/46 |
| 6,213,942 B1 * | 4/2001 | Flach et al. ................. 600/300 |
| 6,443,890 B1 * | 9/2002 | Schulze et al. ............. 600/300 |
| 6,453,195 B1 * | 9/2002 | Thompson ..................... 607/3 |
| 6,480,745 B2 * | 11/2002 | Nelson et al. ................ 607/60 |
| 6,497,655 B1 * | 12/2002 | Linberg et al. ............. 600/300 |
| 2002/0013613 A1 * | 1/2002 | Haller et al. ................. 607/60 |

* cited by examiner

*Primary Examiner*—Mark Bockelman

(57) ABSTRACT

A system and method for remotely controlling the stimulation therapy for neurological, neuropsychiatric and urological disorders, comprises an implantable lead-receiver and an external stimulator with two-way wireless communication capability, through a server. Proximity sensing of an implanted coil and feedback regulation of stimulation pulses is provided through an implanted magnet and circuitry in the external stimulator. The external stimulator comprises predetermined (pre-packaged) programs for neuromodulation therapy. Some of these pre-packaged programs are "locked-out" to the patient, and can be activated remotely via a server by the physician. A physician can also set up a library of the therapy programs to be executed over a set period of time. The physician can also interrogate remotely, the stimulation therapy setting on a a server or a hand-held device, through a server.

24 Claims, 24 Drawing Sheets

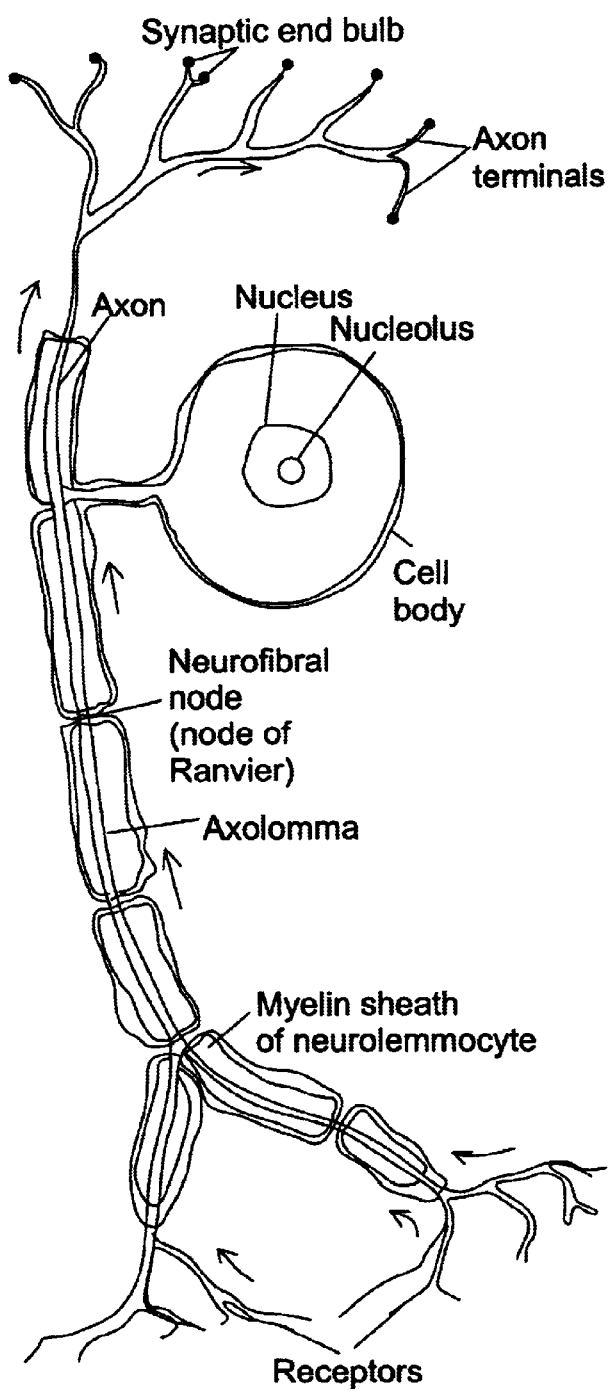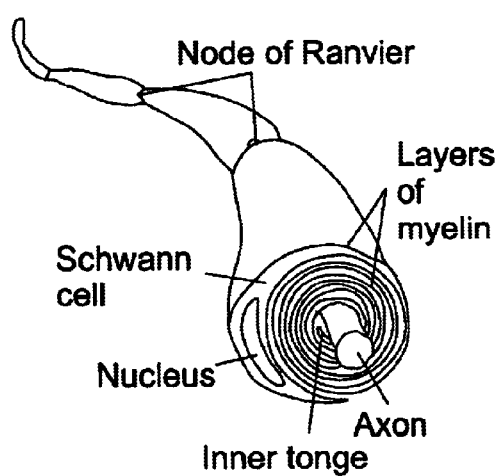
FIG. 9A
FIG. 9B

METHOD AND SYSTEM FOR NEUROMODULATION THERAPY USING EXTERNAL STIMULATOR WITH WIRELESS COMMUNICATION CAPABILITES

FIELD OF THE INVENTION

The present invention relates to wireless communication capability of an external stimulator for neuromodulation, more specifically an external stimulator for neuromodulation therapy for urological, neurological, and neuropsychiatric disorders, having two-way wireless communication through a server.

BACKGROUND OF THE INVENTION

Biological and human clinical research has shown utility of electrical nerve stimulation therapy for urinary incontinence and a broad group of neurological disorders. This invention is directed to remotely controlling the stimulation therapy for these disorders, utilizing an implanted lead-receiver, and an external stimulator with predetermined (pre-packaged) stimulation programs. Some of the predetermined programs may be manually operated, but some programs are locked-out to the patient. These patient locked-out programs can be accessed by the physician either in person via a password or remotely. The remote activation of these programs is via the wireless Internet server, communicating with an external controller using a wireless interface. A physician situated remotely is also able to activate predetermined programs, as well as, interrogate the external stimulation devices of his/her patients. In addition, a physician is able to change which programs are accessible to the patient.

Urinary Incontinance

In considering first, the background of urinary urge incontinence. FIG. 1 shows a sagittal section of the human female pelvis showing the bladder 10 and urethra 13, in relation to other anatomic structures. Urinary continence requires a relaxed bladder during the collecting phase and permanent closure of the urethra 13, whereas at micturition (urination), an intravesical pressure above the opening pressure of the simultaneously relaxing urethra has to be generated. These functions of the bladder 10 and urethra 13 are centrally coordinated and non-separable. At bladder filling, the sensation of urge is mediated by slowly adapting mechanoreceptors in the bladder wall and the same receptors provide the triggering signal for micturition and the main driving force for a sustained micturition contraction. The mechanoreceptors are, technically speaking, tension receptors. It has been found that they respond equally well to tension increases induced passively by bladder filling and those induced actively by a detrusor contraction. These receptors have high dynamic sensitivity and are easily activated by external pressure transients, as may occur during coughing or tapping of the abdominal wall. Their faithful response to active changes in bladder pressure is well illustrated.

When sufficiently activated, the mechanorecptors trigger a coordinated micturition reflex via a center in the upper pons 88, as depicted schematically in FIG. 2. The reflex detrusor 92 (muscle in the wall of the urinary bladder) contraction generates an increased bladder pressure and an even stronger activation of the mechanoreceptors. Their activity in turn reinforces the pelvic motor output to the bladder 10, which leads to a further increase in pressure and more receptor activation and so on. In this way, the detrusor 92 contraction is to a large extent self generating once initiated. Such a control mechanism usually is referred to as a positive feedback, and it may explain the typical all-or-nothing behavior of the parasympathetic motor output to the bladder 10. Once urine enters the urethra, the contraction is further enhanced by reflex excitation from urethral receptors. Quantitatively, the bladder receptors are most important.

A great advantage of the positive feedback system is that it ascertains a complete emptying of the bladder 10 during micturition. As long as there is any fluid left in the lumen, the intravesical pressure will be maintained above the threshold for the mechanoreceptors and thus provide a continuous driving force for the detrusor 92. A drawback with this system is that it can easily become unstable. Any stimulus that elicits a small burst of impulses in mechanoreceptor afferents may trigger a fullblown micturition reflex. To prevent this from happening during the filling phase, the neuronal system controlling the bladder is equipped with several safety devices both at the spinal and supraspinal levels.

The best-known spinal mechanism is the reflex control of the striated urethral sphincter 90, which increases its activity in response to bladder mechanoreceptor activation during filling. An analogous mechanism is Edvardsen's reflex, which involves machanoreceptor activation of inhibitory sympathetic neurons to the bladder. The sympathetic efferents have a dual inhibitory effect, acting both at the postganglionic neurons in the vesical ganglia and directly on the detrusor muscle of the bladder 92. The sphincter and sympathetic reflexes are automatically turned off at the spinal cord level during a normal micturition. At the supraspinal level, there are inhibitory connections from the cerebral cortex and hypothalamus to the pontine micturition center. The pathways are involved in the voluntry control of continance. Other inhibitory systems seem to orignate from the pontine and medullary parts of the brainstem with at least partly descending connections.

Bladder over-activity and urinary urge incontinance may result from an imbalance between the excitatory positive feedback system of the bladder 10 and inhibitory control systems causing a hyperexcitable voiding reflex. Such an imbalance may occur after macroscopic lesions at many sites in the nervous system or after minor functional disturbances of the excitatory or inhibitory circuits. Urge incontinence due to detrusor instability seldom disappears spontaneoulsly. The symptomatic pattern also usually is consistent over long periods.

Based on clinical experience, subtypes of urge incontinance include, Phasic detrusor instability and uninhibited overactive bladder. Phasic detrusor instability is characterized by normal or increased bladder sensation, phasic bladder contractions occurring spontaneously during bladder filling or on provocation, such as by rapid filling, coughing, or jumping. This condition results from a minor imbalance between the bladder's positive-feedback system and the spinal inhibitory mechanisms. Uninhibited overactive bladder is characterized by loss of voluntary control of micturition and impairment of bladder sensation. The first sensation of filling is experienced at a normal or lowered volume and is almost immediately followed by involuntary micturition. The patient does not experience a desire to void until she/he is already voiding with a sustained detrusor contraction and a concomitant relaxation of the urethra, i.e., a well-coordinated micturitiori reflex. At this stage, she/he is unable to interrupt micturition voluntarily. The sensory disturbance of these subjects is not in the periphery, at the level of bladder mechanoreceptors, as the micturition reflex occurs at normal or even small bladder volumes. More likely, the suprapontine sensory projection to the cortex is affected. Such a site is consistent with the coordinated micturition and the lack of voluntary control. The uninhibited overactive bladder is present in neurogenic dysfunction.

Patients with stress and urge incontinence are difficult to treat adequately. Drug treatment often is insufficient and, even when effective, does not lead to restoration of a normal micturition pattern. Since bladder over-activity results from defective central inhibition, it seems logical to improve the situation by reinforcing some other inhibitory system. Successful therapy of the urge component does not influence the stress incontinence. While an operation for stress incontinence sometimes results in deterioration of urgency. Electrostimulation is a logical alternative in mixed stress and urge incontinence, since the method improves urethral closure as well as bladder control Neuromodulation is a technique that uses electrical stimulation of the sacral nerves 85, (a general diagram of spinal cord and sacral nerves 85 is shown in FIG. 3). The aim of this treatment modality is to achieve detrusor 92 inhibition by chronic electrical stimulation of afferent somatic sacral nerve fibers 85 via implanted electrodes connected to a subcutaneously placed pulse generation means.

The rationale of this treatment modality is based on the existence of spinal inhibitory systems that are capable of interrupting a detrusor 92 contraction. Inhibition can be achieved by electrical stimulation of afferent anorectal branches of the pelvic nerve, afferent sensory fibers in the pudendal nerve and muscle afferents from the limbs. Most of these branches and fibers reach the spinal cord via the dorsal roots of the sacral nerves 85. Of the sacral nerve roots the S3 root is the most practical for use in chronic electrical stimulation. In neuromodulation, the entire innervation system should be intact. As shown schematically in FIG. 4, the procedure consists of placing electrodes 61,62 in one of the sacral foramen as close to the pelvic plexus and pudendal nerve as possible and connecting the lead 59 with a means for electrical stimulation 49. An anchoring sleeve 15 may be used for securing the lead.

The hypothesis behind neuromodulation of the sacral roots (sensory and motor) is to correct, by the use of regulating electrical impulses, the dys-synergic activities of the cholinergic, adrenergic, and motor reflex pathways that initiate vesical storage and micturition. Although some theories have been developed that explain the effects of neuromodulation, most of the results are based on empiric findings in human studies. Some animal experiments and electrophysiologic studies in humans show there is a spinal inhibitory action through the afferent branches of the pelvic and pudendal nerves. It is not clear whether neuromodulation primarily influences the micturiction center located near the thalamus 25. Some maintain that there is a direct correction of the dys-synergis of the pelvic floor (pudendal nerve) by influencing the abnormal contractility of the pelvic floor.

A neurophysiological explanation for the effectiveness of this treatment modality in detrusor instability is based on animal experiments and electrophysiological studies in humans. Electrical stimulation for the treatment of urinary incontinence has evolved over the past 40 years. The mechanism of action of electrical stimulation was investigated initially in animal models. Over 100 years ago, Griffiths demonstrated relaxation of a contracted detrusor during stimulation of the proximal pudendal nerve in the cat model and further work clarified the role of pudendal afferents in relation of the detrusor 92. Spinal inhibitory systems capable of interrupting a detrusor 92 contraction can be activated by electrical stimulation of afferent anorectal branhes of the pelvic nerve, afferent sensory fibers in the pudendal nerve and muscle afferents from the limbs. The effectiveness of neuromodulation in humans has been objectively demonstrated by urodynamic improvement, expecially in light of the fact that such effects have not been noted in drug trials.

Neuromodulation also acts on neural reflexes but does so internally by stimulation of the sacral nerves 85. Sacral nerve 85 stimulation is based on research dedicated to the understanding of the voiding reflex as well as the role and influence of the sacral nerves 85 on voiding behavior. This research led to the development of a technique to modulate dysfunctional voiding behavior through sacral nerve stimulation. It is thought that sacral nerve stimulation induces reflex mediated inhibitory effects on the detrusor 92 through afferent and/or efferent stimulation of the sacral nerves 85. Even though the precise mechanism of action of electrical stimulation in humans is not fully understood, it has been shown that sensory input traveling through the pudendal nerve can inhibit detrusor activity in humans. Most experts believe that non-implanted electrical stimulation works by stimulating the pudendal nerve afferents, with the efferent outflow causing contraction of the striated pelvic musculature. There is also inhibition of inappropriate detrusor activity.

In summary, the rationale for neuromodulation in the treatment of such patients is the observation that stimulation of the sacral nerves via electrical stimulation can inhibit inappropriate neural reflex behavior.

Neurological and Neuropsychiatric Disorders

Moving now to the background of neurological disorders. Adjunct therapy for neurological disorders such as partial complex epilepsy, generalized epilepsy, depression, Alzheimer's disease, and several other disorders related to neuromodulation of the vagus nerve. Biological research has shown beneficial medical effects of vagus nerve stimulation (VNS) for patients with the above disorders.

Vagus nerve stimulation, and the profound effects of electrical stimulation of the vagus nerve on central nervous system (CNS) activity, extends back to the 1930's. Medical studies in clinical neurobiology have advanced our understanding of anatomic and physiologic basis of the beneficial neurologic effects of chronic vagus nerve stimulation.

Some of the somatic interventions for the treatment of depression and the like, include electroconvulsive therapy (ECT), transcranical magnetic stimulation, vagus nerve stimulation, and deep brain stimulation. The vagus nerve 54 is the 10th cranial nerve, and is a direct extension of the brain. FIG. 5, shows a diagram of the brain and spinal cord, with its relationship to the vagus nerve 54 and the nucleus tractus solitarius 14. FIG. 6 shows a diagram of base of the brain, showing the relationship of the vagus nerve with the other eleven cranial nerves.

Vagus nerve stimulation is a means of directly affecting central function and is less invasive than deep brain stimulation (DBS). As shown in FIG. 7, cranial nerves have both afferent pathway 19 (inward conducting nerve fibers which convey impulses toward the brain) and efferent pathway 21

(outward conducting nerve fibers which convey impulses to an effector). The vagus nerve 54 is composed of 80% afferent sensory fibers carrying information to the brain from the head, neck, thorax, and abdomen. The sensory afferent cell bodies of the vagus reside in the nodose ganglion and relays information to the nucleus tractus solitarius (NTS).

As shown schematically in FIG. 8, the nucleus of the solitary tract 14 relays this incoming sensory information to the rest of the brain through three main pathways; 1) an autonomic feedback loop, 2) direct projection to the reticular formation in the medulla, and 3) ascending projections to the forebrain largely through the parabrachial nucleus 20 (PBN) and the locus ceruleius 22 (LC). The PBN sits adjacent to the LC (FIG. 5). The PBN/LC sends direct connections to every level of the forebrain, including the hypothalamus 26, and several thalamic regions that control the insula and orbitofrontal 28 and prefrontal cortices. Perhaps important for mood regulation, the PBN/LC has direct connections to the amygdala 27 and the bed nucleus of the stria terminalis—structures that are implicated in emotion recognition and mood regulation.

In sum, incoming sensory (afferent) connections of the vagus nerve 54 provide direct projections to many of the brain regions implicated in neurologic and neuropsychiatric disorders. These connections reveal how vagus nerve 54 stimulation is a portal to the brainstem and connected regions. These circuits likely account for the beneficial neurologic and neuropsychiatric effects of the vag us nerve stimulation.

Increased activity of the vagus nerve 54 is also associated with the release of more serotonin in the brain. Much of the pharmacologic therapy for treatment of migraines is aimed at increasing the levels of serotonin in the brain. Therefore, non-pharmacologic therapy of electrically stimulating the vagus nerve 54 would have benefits for adjunct treatment of migraines also.

The vagus nerve 54 provides an easily accessible, peripheral route to modulate central nervous system (CNS) function. Other cranial nerves can be used for the same purpose, but the vagus nerve 54 is preferred because of its easy accessibility. In the human body there are two vagus nerves (VN), the right VN and the left VN. Each vagus nerve is encased in the carotid sheath along with the carotid artery and jugular vein. The innervation of the right and left vagus nerves is different. The innervation of the right vagus nerve is such that stimulating it results in profound bradycardia (slowing of the heart rate). The left vagus nerve has some innervation to the heart, but mostly innervates the visceral organs such as the gastrointestinal tract. It is known that stimulation of the left vagus nerve does not cause any significant deleterious side effects.

Most nerves in the human body are composed of thousands of fibers, of different sizes designated by groups A, B and C, which carry signals to and from the brain. The vagus nerve 54, for example, may have approximately 100,000 fibers of the three different types, each carrying signals. Each axon or fiber (shown in FIG. 9A) of that nerve conducts only in one direction, in normal circumstances. The A and B fibers are myelinated (i.e., have a myelin sheath, constituting a substance largely composed of fat, as shown in FIG. 9B), whereas the C fibers are unmyelinated.

A commonly used nomenclature for peripheral nerve fibers, using Roman and Greek letters, is given in the table below:

| Group | External Diameter ($\mu$m) | Conduction Velocity (m/sec) |
| --- | --- | --- |
| Myelinated Fibers | | |
| A$\alpha$ or IA | 12–20 | 70–120 |
| A$\beta$: IB | 10–15 | 60–80 |
| II | 5–15 | 30–80 |
| A$\gamma$ | 3–8 | 15–40 |
| A$\delta$ or III | 3–8 | 10–30 |
| B | 1–3 | 5–15 |
| Unmyelinted fibers | | |
| C or IV | 0.2–1.5 | 0.5–2.5 |

The diameters of group A and group B fibers include the thickness of the myelin sheaths. Group A is further subdivided into alpha, beta, gamma, and delta fibers in decreasing order of size. There is some overlapping of the diameters of the A, B, and C groups because physiological properties, especially the form of the action potential, are taken into consideration when defining the groups. The smallest fibers (group C) are unmyelinated and have the slowest conduction rate, whereas the myelinated fibers of group B and group A exhibit rates of conduction that progressively increase with diameter. Group B fibers are not present in the nerves of the limbs; they occur in white rami and some cranial nerves.

Compared to unmyelinated fibers, myelinated fibers are typically larger, conduct faster, have very low stimulation thresholds, and exhibit a particular strength-duration curve or respond to a specific pulse width versus amplitude for stimulation. The A and B fibers can be stimulated with relatively narrow pulse widths, from 50 to 200 microseconds ($\mu$s), for example. The A fiber conducts slightly faster than the B fiber and has a slightly lower threshold. The C fibers are very small, conduct electrical signals very slowly, and have high stimulation thresholds typically requiring a wider pulse width (300–1,000 $\mu$s) and a higher amplitude for activation. Selective stimulation of only A and B fibers is readily accomplished. The requirement of a larger and wider pulse to stimulate the C fibers, however, makes selective stimulation of only C fibers, to the exclusion of the A and B fibers, virtually unachievable inasmuch as the large signal will tend to activate the A and B fibers to some extent as well.

The vagus nerve is composed of somatic and visceral afferents and efferents. Usually, nerve stimulation activates signals in both directions (bi-directionally). It is possible, however, through the use of special electrodes and waveforms, to selectively stimulate a nerve in one direction only (unidirectionally). The vast majority of vagus nerve fibers are C fibers, and a majority are visceral afferents having cell bodies lying in masses or ganglia in the skull. The central projections terminate largely in the nucleus of the solitary tract 14 which sends fibers to various regions of the brain (e.g., the hypothalamus 26, thalamus 25, and amygdala 27).

In summary the basic premise of vagus nerve 54 stimulation for relief of neurological disorders is that vagus visceral afferents have a diffuse central nervous system (CNS) projection, and activation of these pathways has a widespread effect on neuronal excitability.

PRIOR ART

One form of prior art neuromodulation therapy is generally directed to an implantable pulse generator system. In such a system, the communication is generally performed via a modified personnel computer and a programming wand.

Prior art wireless communication for medical stimulation devices includes, U.S. Pat. No. 5,759,199 (Snell et al) which is directed to ambulatory monitoring and programming of an implantable medical device. The system disclosed enables wireless communication between the programmer/analyzer and the implantable medical device.

U.S. Pat. No. 5,978,713 (Prutchi) is primarily directed to telemetry of information from an implant that is generated from atrial and ventricular endocardial leads to an external programmer.

U.S. Pat. No. 5,997,476 (Brown) is directed to communicating information to an individual and for remotely monitoring the individual. The system of the '476 patent includes a server and a remote interface for entering in the server a set of queries to be answered by the individual. The disclosed system includes a remotely programmable apparatus connected to the server via a communication network.

U.S. Pat. No. 5,458,122 (Hethuin) is directed to the wireless transmission of surface EKG signals to a remote location via transmission equipment components held onto the body of the patient.

One form of prior art for neuromodulation therapy, generally includes implantable pulse generators. U.S. Pat. Nos. 4,702,254, 4,867,164 and 5,025,807 (Zabara) generally disclose animal research and experimentation related to epilepsy and the like and are directed to stimulating the vagus nerve by using "pacemaker-like" technology, such as an implantable pulse generator. The pacemaker technology concept consists of a stimulating lead connected to a pulse generator (containing the circuitry and DC power source) implanted subcutaneous or submuscularly, somewhere in the pectoral or axillary region, with an external personal computer (PC) based programmer. Once the pulse generator is programmed for the patient, the fully functional circuitry and power source are fully implanted within the patient's body. In such a system, when the battery is depleted, a surgical procedure is required to disconnect and replace the entire pulse generator (circuitry and power source). These patents neither anticipate practical problems of an inductively coupled system for adjunct therapy of epilepsy, nor suggest solutions to the same for an inductively coupled system for adjunct therapy of partial complex or generalized epilepsy.

U.S. Pat. No. 5,215,086 (Terry, Jr. et al) is directed to the use of implantable pulse generator technology for treating and controlling migraine, by stimulating the vagus nerve of a patient by an implantable lead and "pacemaker like" device to alleviate the migraine attack.

U.S. Pat. No. 4,771,779 (Tanagho et al) is directed to a system for controlling bladder evacuation, which consists of multiple implanted stimulation systems having electrodes positioned on nerves controlling external sphincter and bladder functions, and electronic control system which transmit to the stimulation systems. In this patent, by having multiple stimulation systems and means of controlling them, the interaction between stimulating the bladder and external sphincter can be controlled.

SUMMARY OF THE INVENTION

The present invention is directed to a system and method for remotely controlling the neuromodulation therapy of urological, neurological, neuropsychiatric disorders. The system comprises an implantable lead-receiver, and an external stimulator with the primary coil on the same packaging. The implanted lead-receiver and the external stimulator are inductively coupled. The external stimulator has two way wireless communication capabilities. This wireless capability is used primarily to exchange the programmed parameters in the stimulator to remotely control the stimulation therapy.

An implanted lead-receiver contains electrodes in contact with the nerve to be stimulated, passive circuitry, and a secondary coil for coupling with an external (primary) coil. The external stimulator comprises a unit, which is about the size of a small cardiac pacemaker on which a coil and pulse generator circuitry with a replaceable power source (battery) module are mounted. The pulse generator battery is the disposable component of the system. An indicator on the external stimulator indicates the battery status, so that the battery can be routinely replaced. Proximity sensing circuitry aids in the optimal placement of the external stimulator coil, in close proximity to the secondary (implanted) coil. The combination of a magnet in the implanted lead-receiver and sensors mounted in the external generator, provide means for proximity sensing and feedback control of pulse stimulus outputs. The feedback circuitry adjusts the output of pulses to ensure proper delivery of electrical stimulation therapy as the primary (external) and secondary (implanted) coils change orientation relative to each other. The external stimulator contains a limited number of pre-determined (pre-packaged) programs consisting of unique combinations of parameters such as pulse amplitude, pulse width, frequency of stimulation, on-time, and off-time.

In one aspect of the invention, the external stimulator communicates wirelessly with a remote server, using a communication protocol such as wireless application protocol (WAP). A physician who may be situated remotely, is able to access information regarding the pulse generation programs that the stimulator is currently using to deliver pulse signals to the patient. The physician can change the therapy to another predetermined program by communicating with the server. The server in turn communicates with the neurostimulator (external pulse generator). The physician can also make relatively "small" variations to existing programs for improvements in therapy being delivered. The communication between physician's handheld device and server, and communication between the server and external neurostimulator utilizes the wireless application protocol (WAP).

In another aspect of the invention, a physician at a remote location, using a wireless handheld device, is able to check the stimulation program execution status of his/her patient population by obtaining a summary report, using secure communication.

In yet another aspect of the invention, the physician is able to set up long-term schedules of stimulation therapy for their patient population, through wireless communication with the server. The server in turn communicates these programs to the neuro-stimulator. For instance, a physician may program an Alzheimer's patient to a stimulation program for two weeks, and program an epilepsy patient to long-term "on", "off" stimulation therapy. Each schedule is securely maintained on the server, and is editable by the physician, and can get uploaded to the patient's stimulator device at a scheduled time. Each device issued to a patient has a unique identification key in order to guarantee secure communication between the wireless server and device.

BRIEF DESCRIPTION OF THE DRAWINGS

For the purpose of illustrating the invention, there are shown in accompanying drawing, forms which are presently preferred, it being understood that the invention is not intended to be limited to the precise arrangement and instrumentalities shown.

FIG. 9A is a diagram of a nerve fiber.

FIG. 9B is a diagram of a nerve fiber showing layers of myelin.

DETAILED DESCRIPTION OF THE INVENTION

The following description is of the current embodiment for carrying out the invention. This description is not to be taken in a limiting sense, but is made merely for the purpose of describing the general principles of the invention. The scope of the invention should be determined with reference to the claims.

The system and method of programmed neuromodulation consists of an implantable lead-receiver and an external stimulator with predetermined (pre-packaged) programs for neuromodulation. The implantable lead-receiver and external stimulator are inductively coupled. The pre-determined programs contain unique combinations of parameters and differ in the aggressiveness of the stimulation therapy. Some of the pre-determined programs are "locked-out" to the patient or caretaker, and can be accessed and controlled by the physician only. The pre-determined programs can be controlled (new programs selected and small modifications made) remotely by the physician, using wireless communication, as described later.

Figure 1:
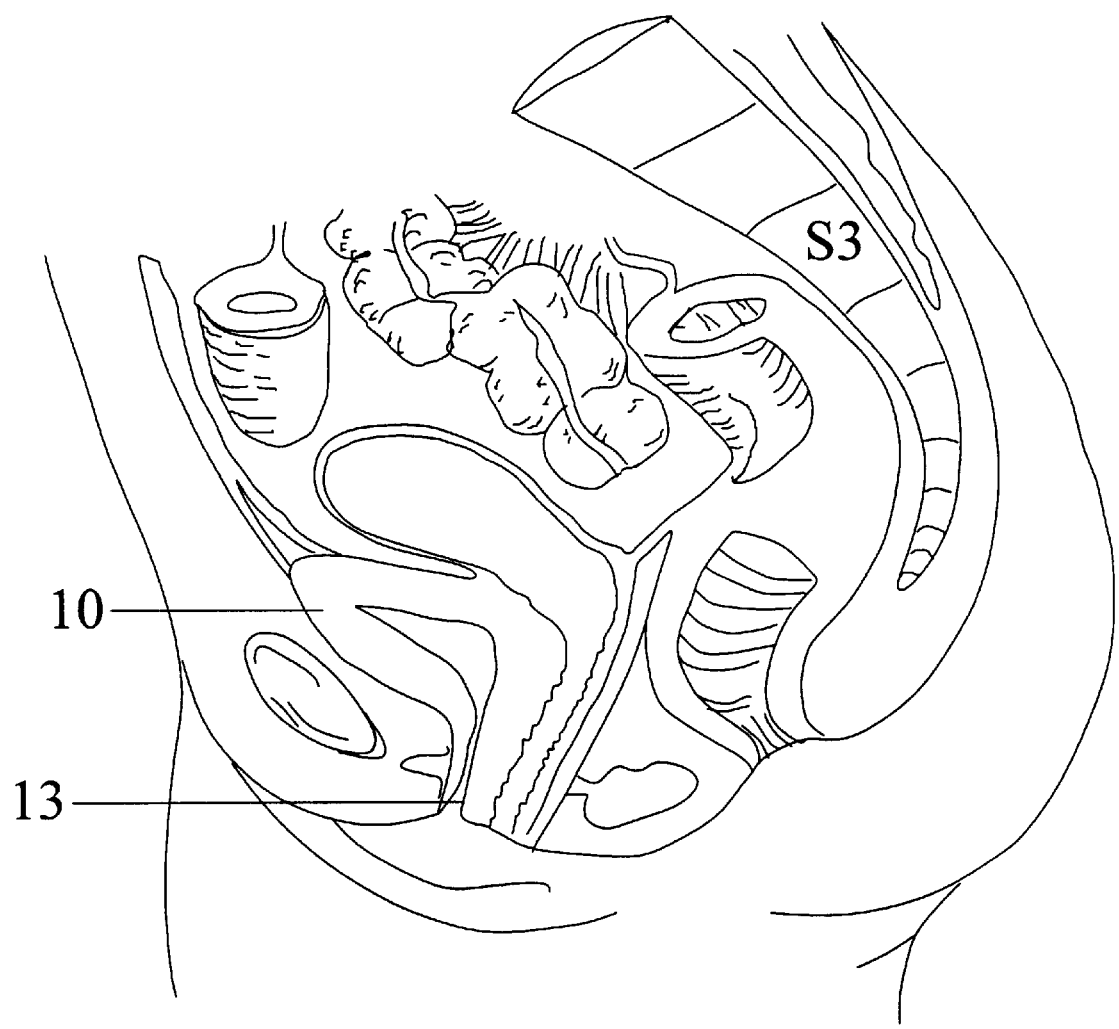
FIG. 1 shows a diagram of the sagittal section of the female pelvis, showing the relationship between various anatomic structures.
Figure 2:
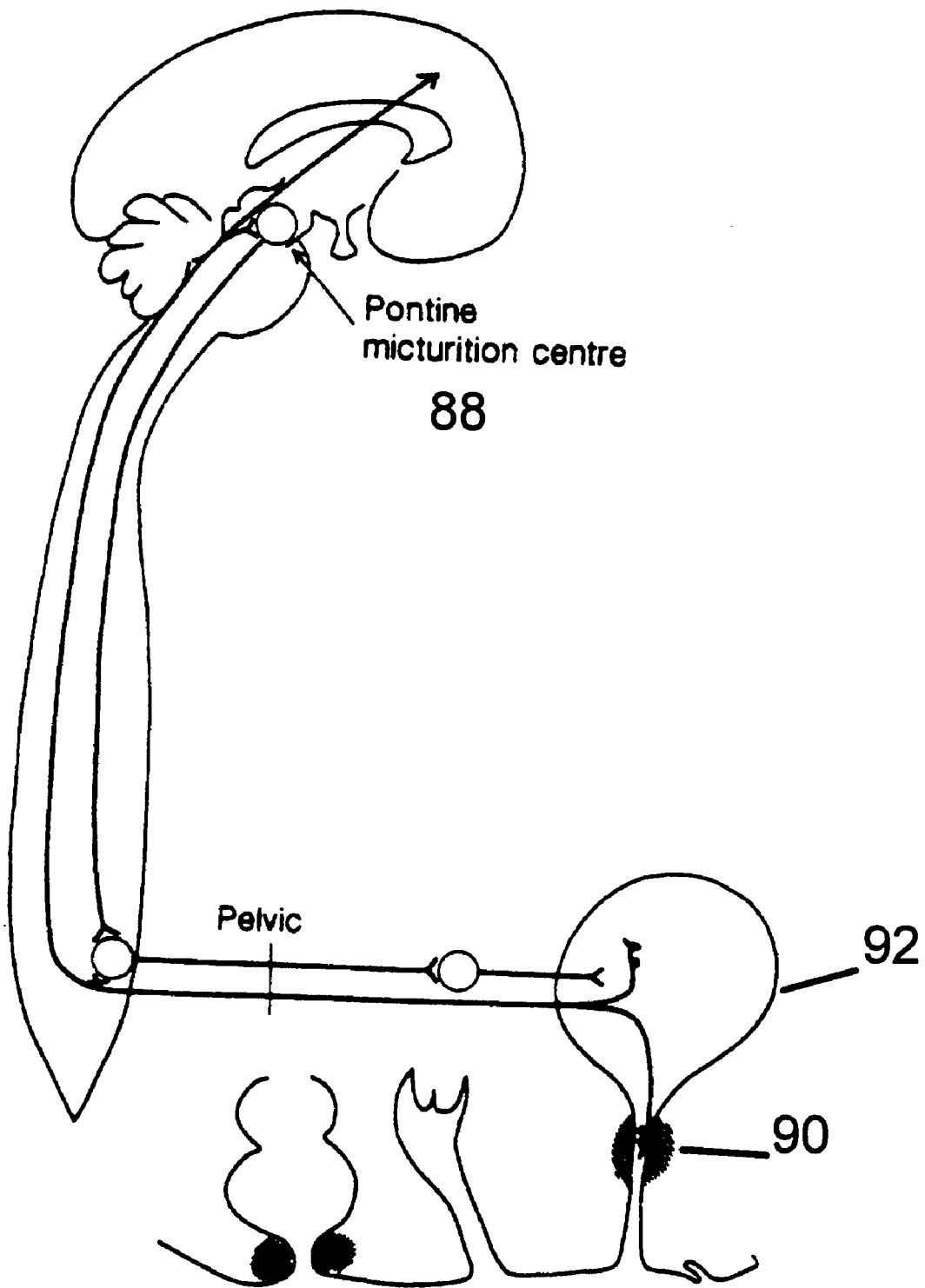
FIG. 2 is a schematic diagram showing physiological control of micturition.
Figure 3:
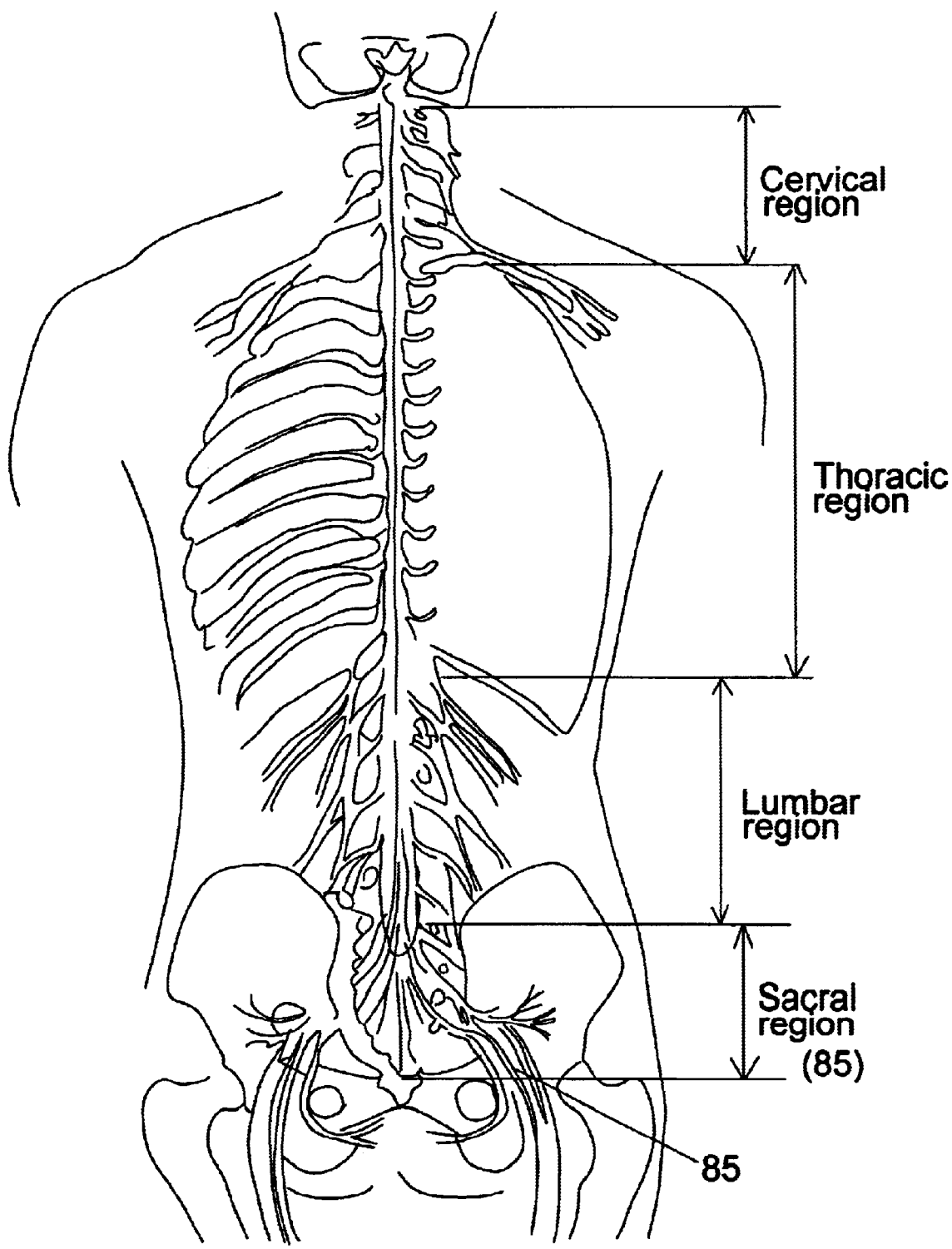
FIG. 3 is a diagram showing anatomic relationships of the spinal nerves and sacral plexus.
Figure 4:
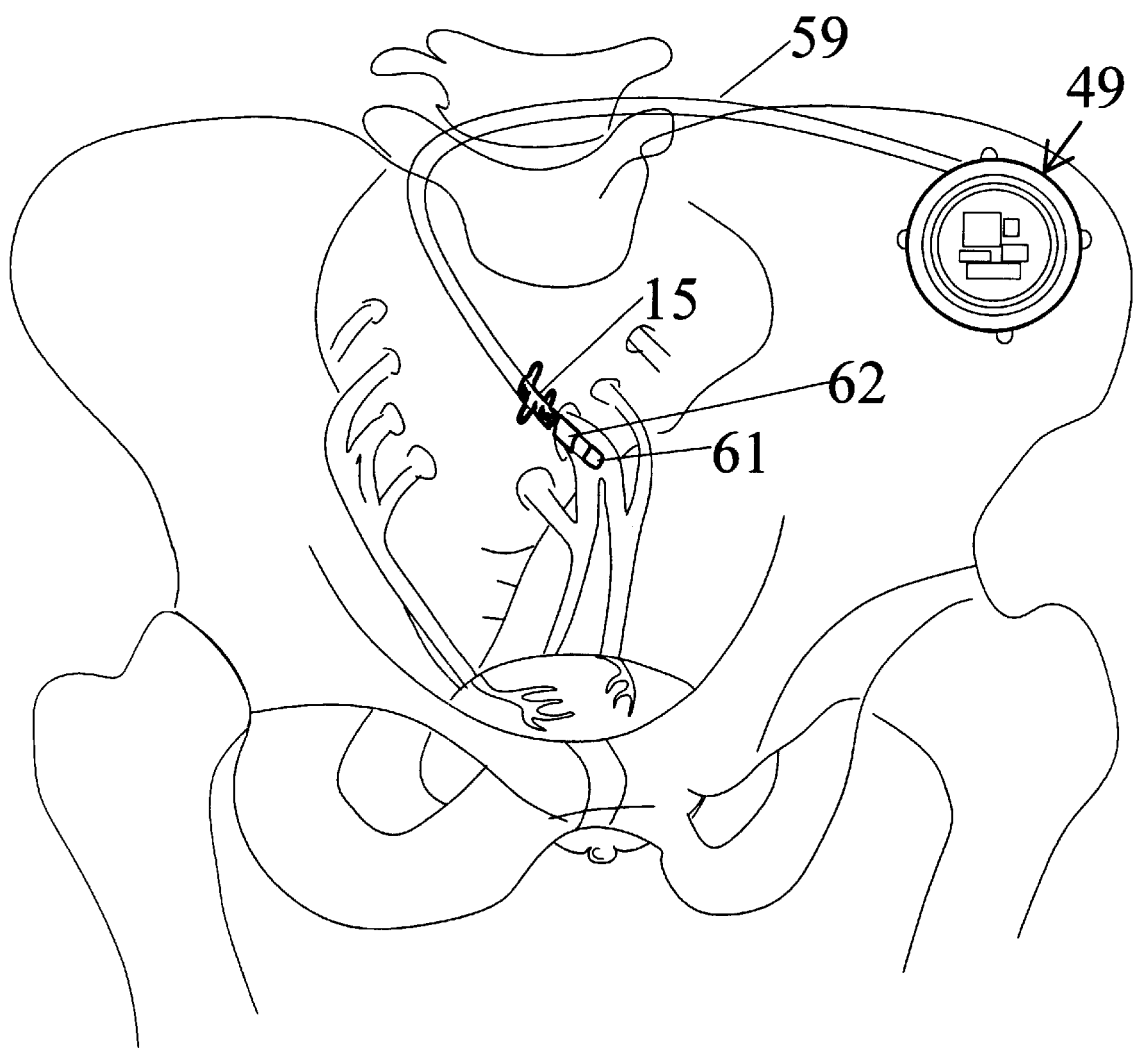
FIG. 4 is a schematic diagram of the sacral region showing electrodes in sacral foraman, and placement of the lead-receiver.
Figure 5:
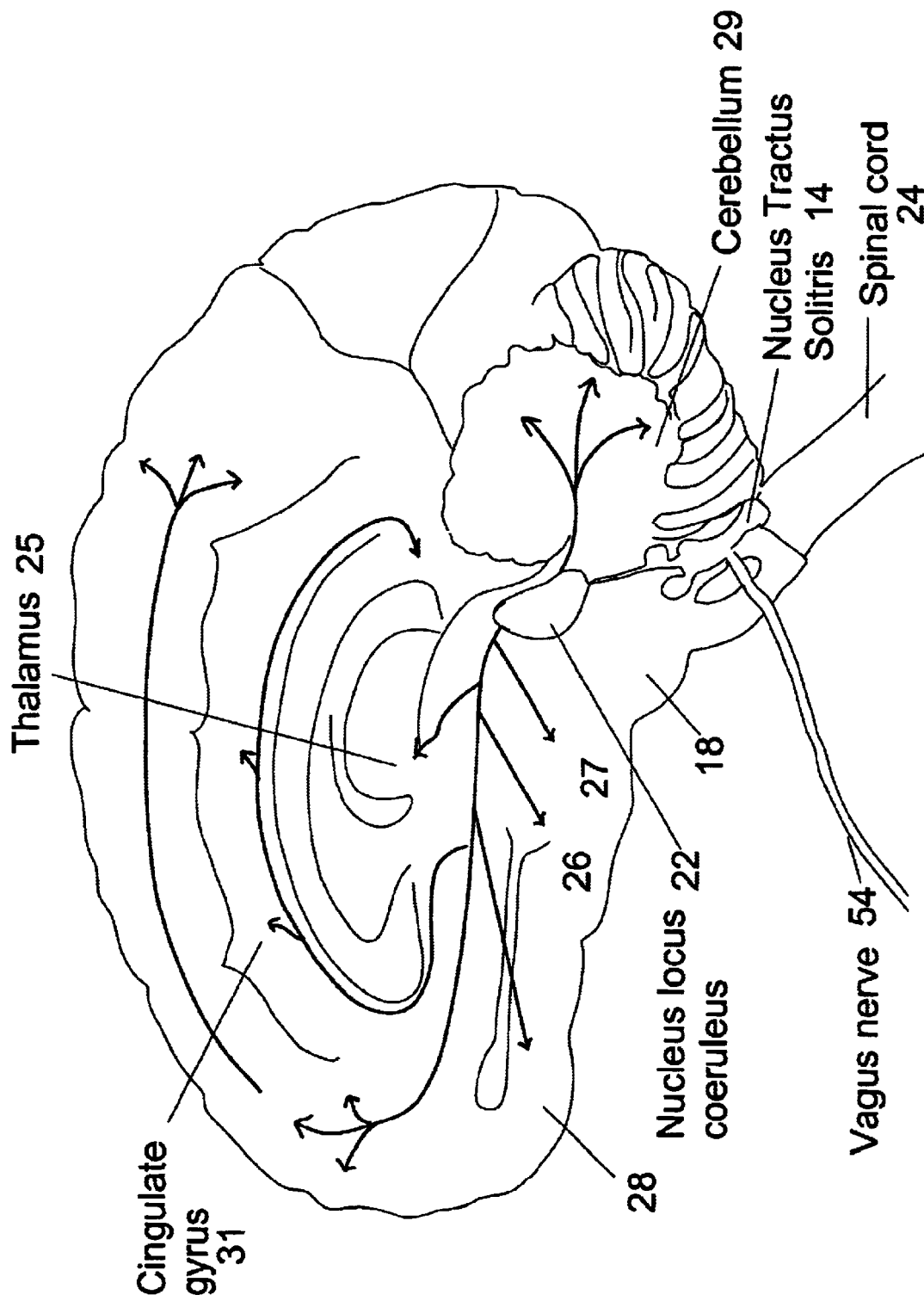
FIG. 5 is a diagram of the lateral view of the brain and spinal cord, with its relationship to the vagus nerve.
Figure 6:
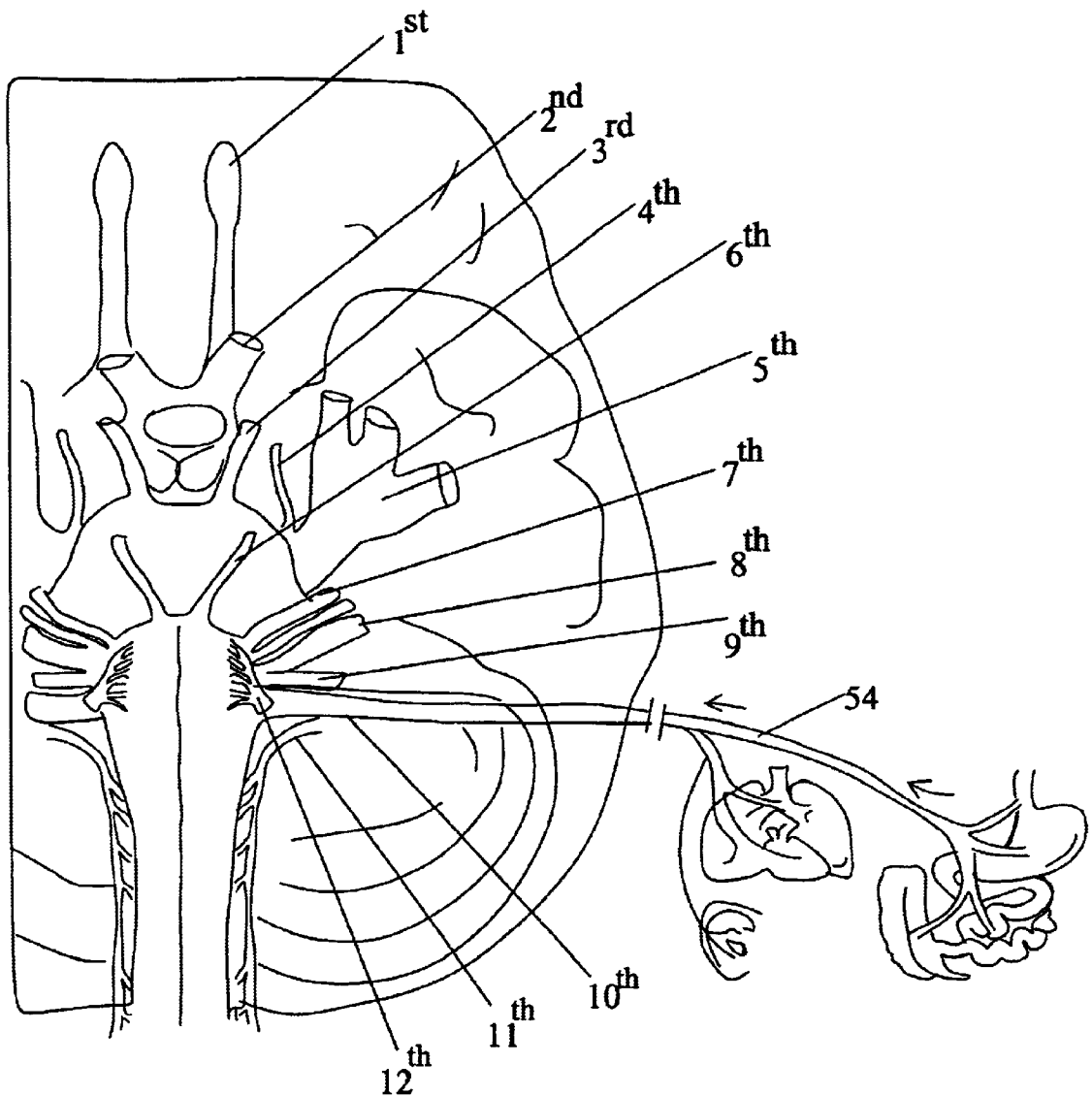
FIG. 6 is a diagram of the base of brain showing the relationship of vagus nerve to the other cranial nerves.
Figure 7:
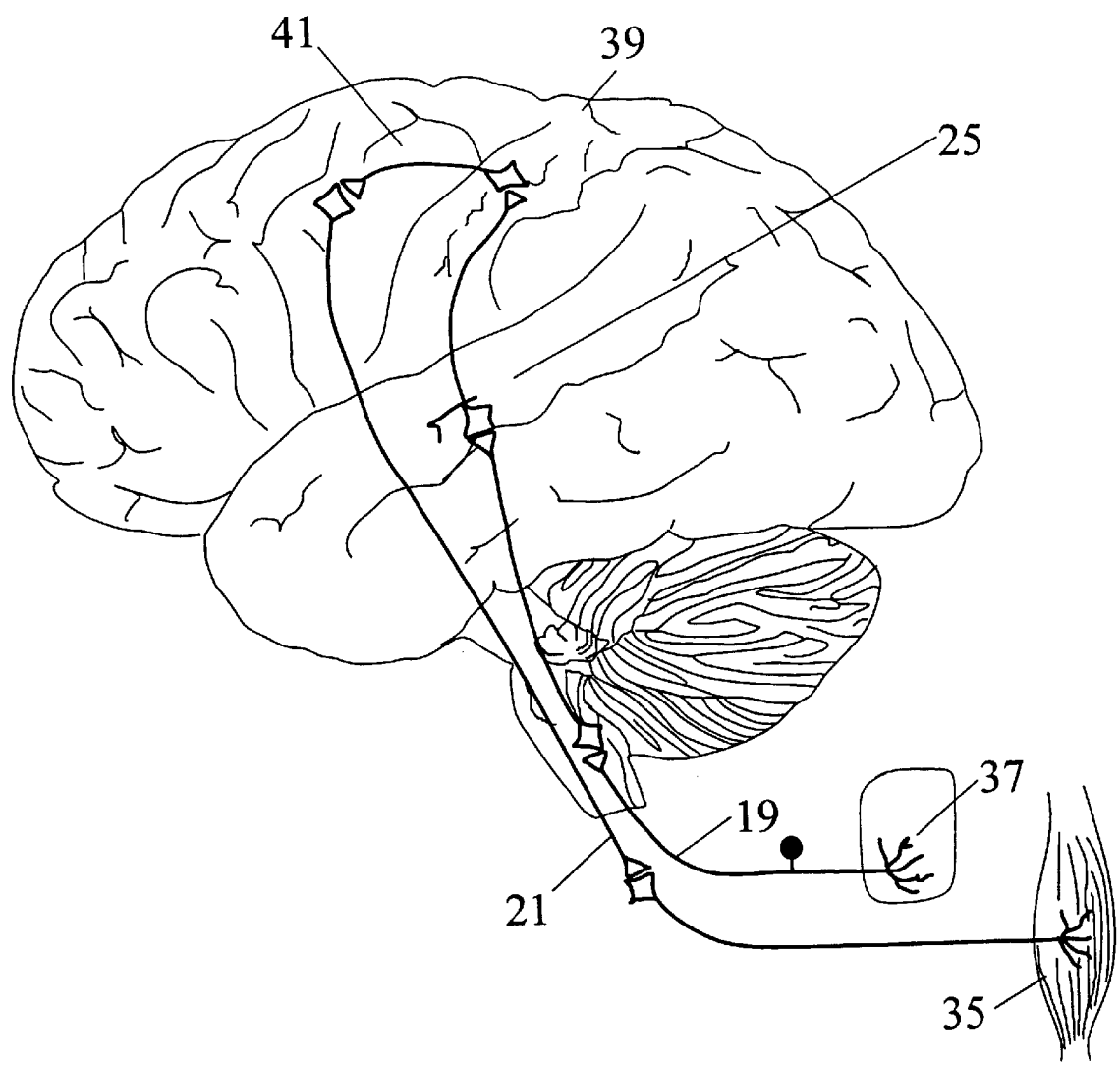
FIG. 7 is a diagram of the brain showing afferent and efferent pathways.
Figure 8:
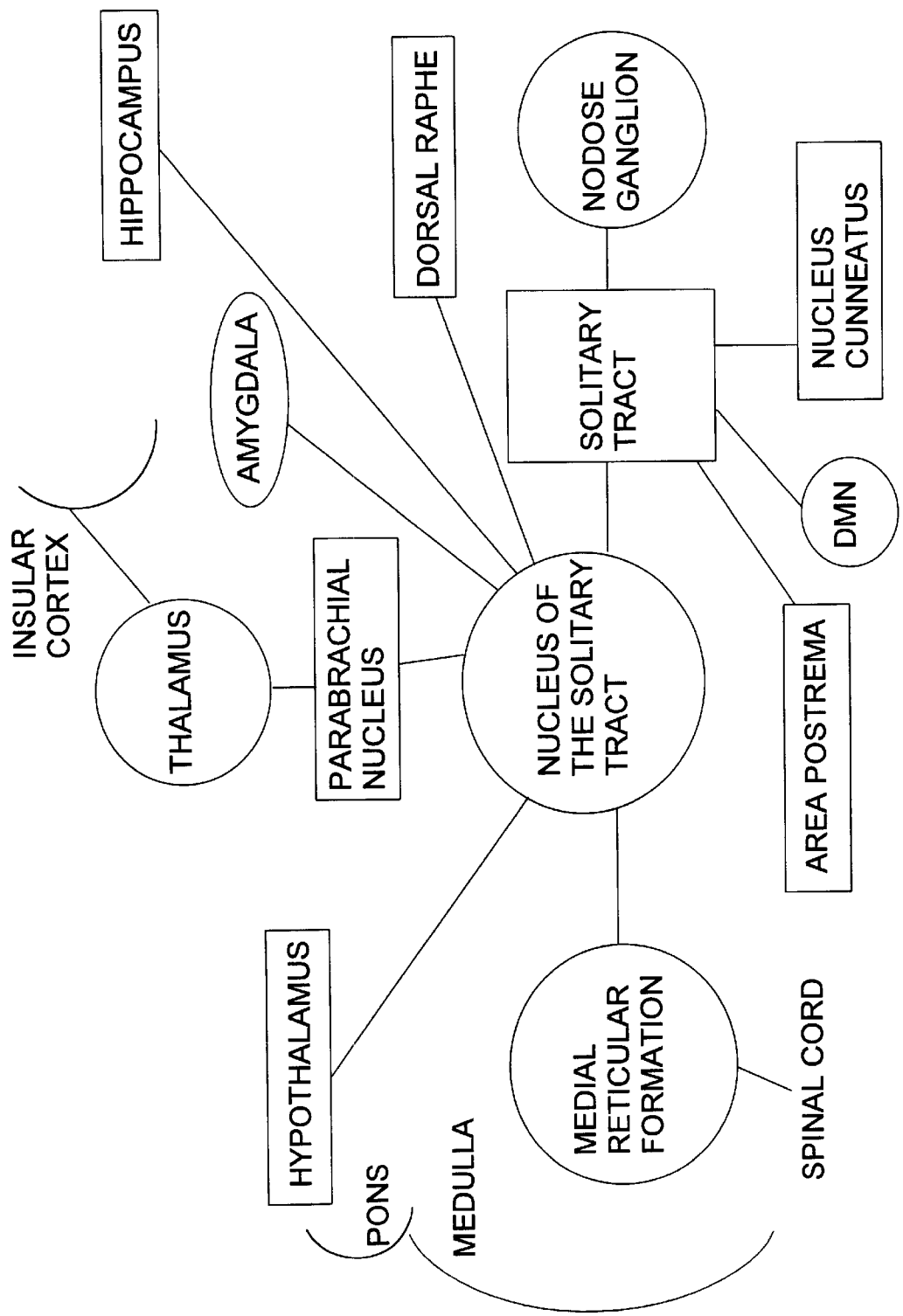
FIG. 8 is a schematic showing relationship of Nucleus of the Solitary Track and how it relays information to other parts of the brain.
Figure 10:
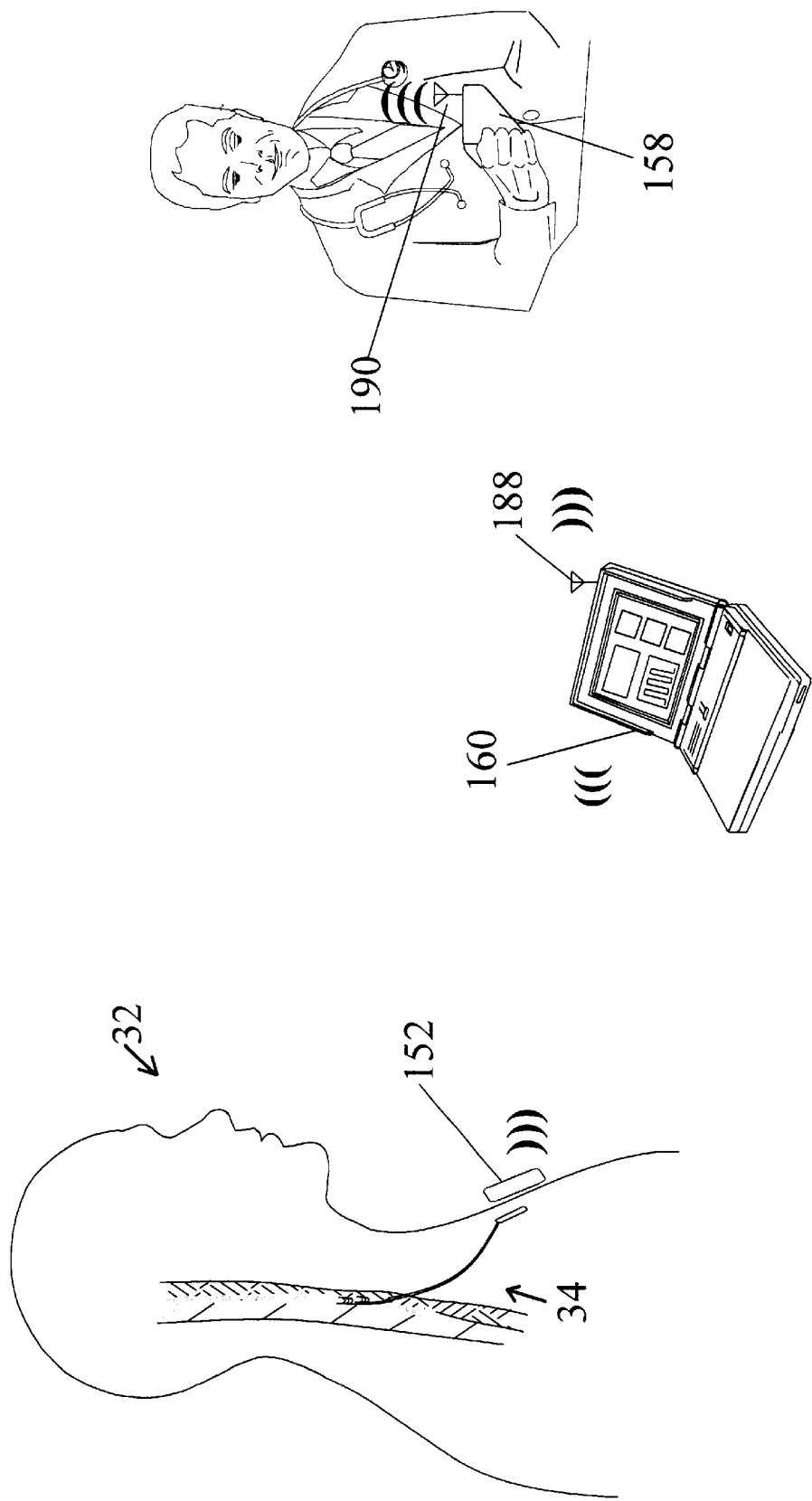
FIG. 10A is a schematic diagram showing the concept of the invention. The placement of the external stimulator is on the upper part of the chest for neurological, and neuropsychiatric applications.
FIG. 10B is a schematic diagram showing the concept of the invention. The placement of the external stimulator is on the lower abdomen for urge incontinance applications.
Figure 10:
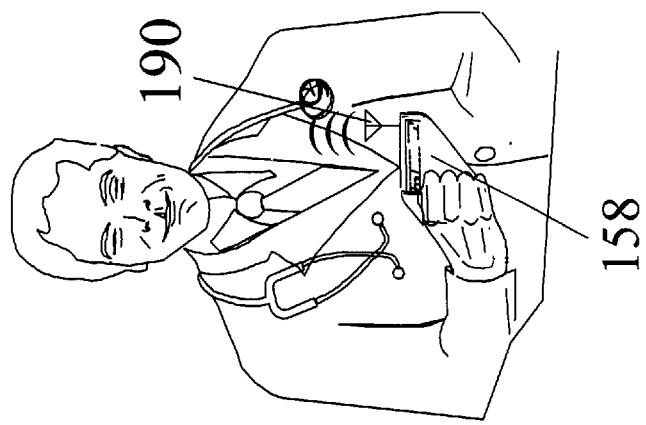
Figure 10:
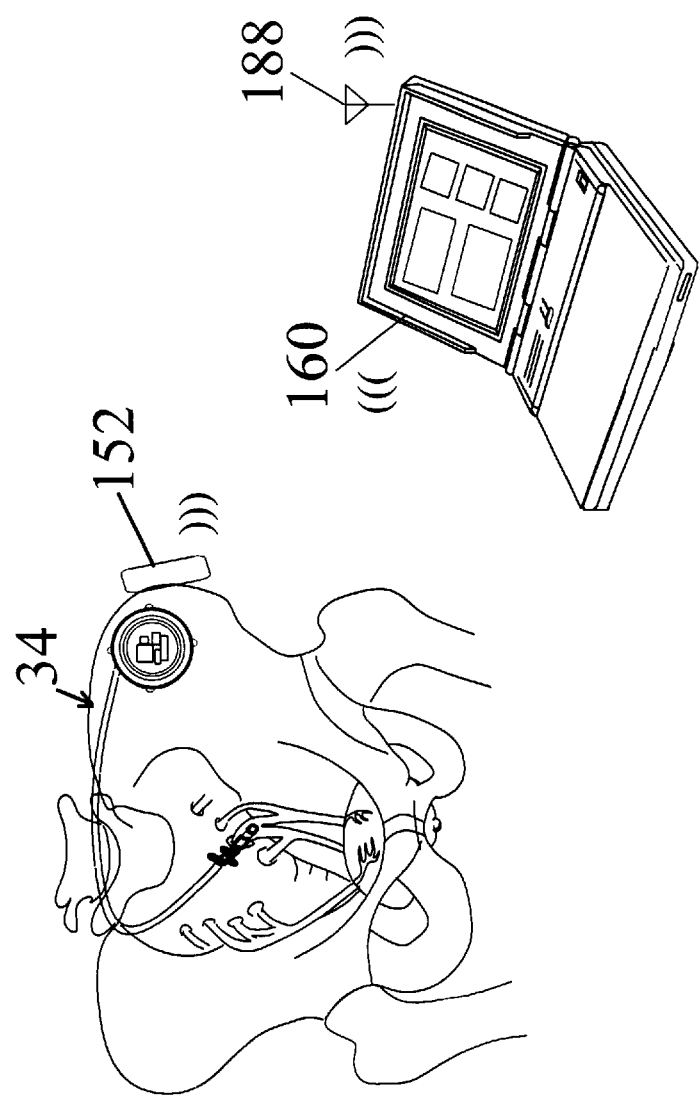

FIGS. 10A and 10B are diagrams which show schematically the overall concept of the invention. As shown in the figures, the placement of the external stimulator (and primary coil) is on the upper part of the chest for neurological applications (FIG. 10A), and on the lower abdomen for urinary incontinence (FIG. 10B) applications. The physician is shown with a hand-held device (PDA) 158, that can communicate remotely with a wireless server 160. The wireless server 160, is typically situated in a central location of the health care provider's facility. The physician can be situated remotely, in the same or another building separated by more than a few hundred feet. The physician has a hand-held device (PDA) 158 that can be used for interrogating the parameters of pulse generator signals for a particular patient, while the physician is mobile. The wireless server 160 can then communicate with the external stimulator device 152, which is physically attached on a patient. Within the body of the patient, on the subcutaneous side of the external stimulator 152, is an implanted lead-receiver 34. The distal end of the implanted lead-receiver 34 has electrodes 161,162 in contact with the nerve to be stimulated. The primary coil of the external stimulator 152 and secondary (subcutaneous) coil of the implanted lead-receiver 34 are inductively coupled.

Figure 11:
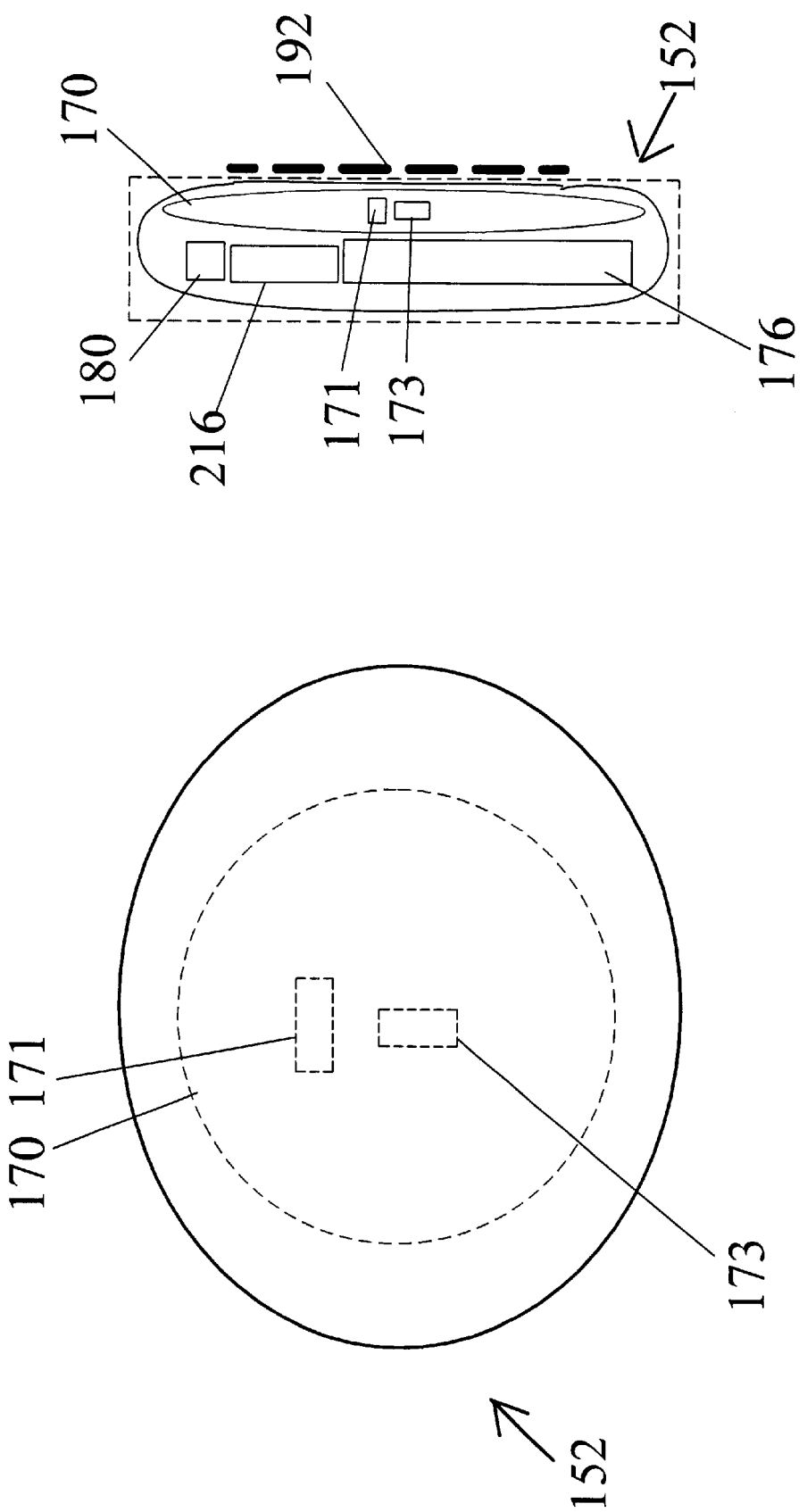
FIG. 11 is a diagram showing the front-view and side-view of the external stimulator and patch.

The external stimulator (pulse generator) package 152, which is about the size and shape of a small cardiac pacemaker, contains a primary coil attached to the housing of the stimulator. FIG. 11 shows a schematic diagram of the external stimulator 152 of the presently preferred embodiment. The end-view shows the components such as external (primary) coil 170, sensors 171, and a patch 175 that connects to the skin 192. The outline of the case of the external stimulator 152 , which enclosed in a case, is also shown in FIG. 11. The sensors help to facilitate the correct placement of the patch, in proximity to the subcutaneous (secondary) coil of the implanted lead-receiver 34.

Figure 12:
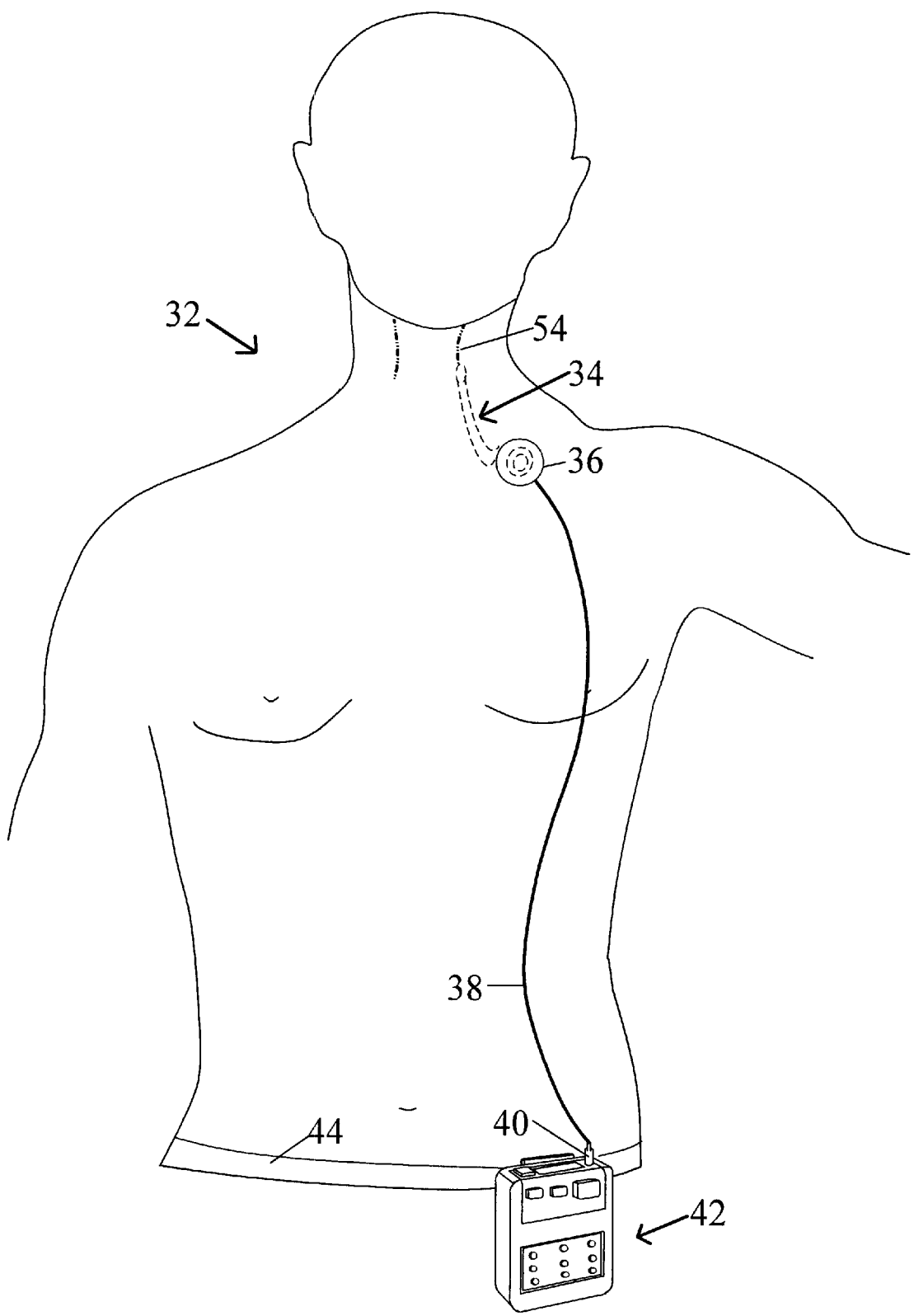
FIG. 12 is a diagram showing an alternative embodiment of an external pulse generator with wire connection to the supercutaneous coil.

FIG. 12 shows a schematic diagram of an alternative embodiment of an external stimulator used for neuromodulation. The pulse generator in this embodiment may be worn on a belt or carried in a pocket. The connection of the external (primary) coil to the stimulator is through a wire.

Figure 13:
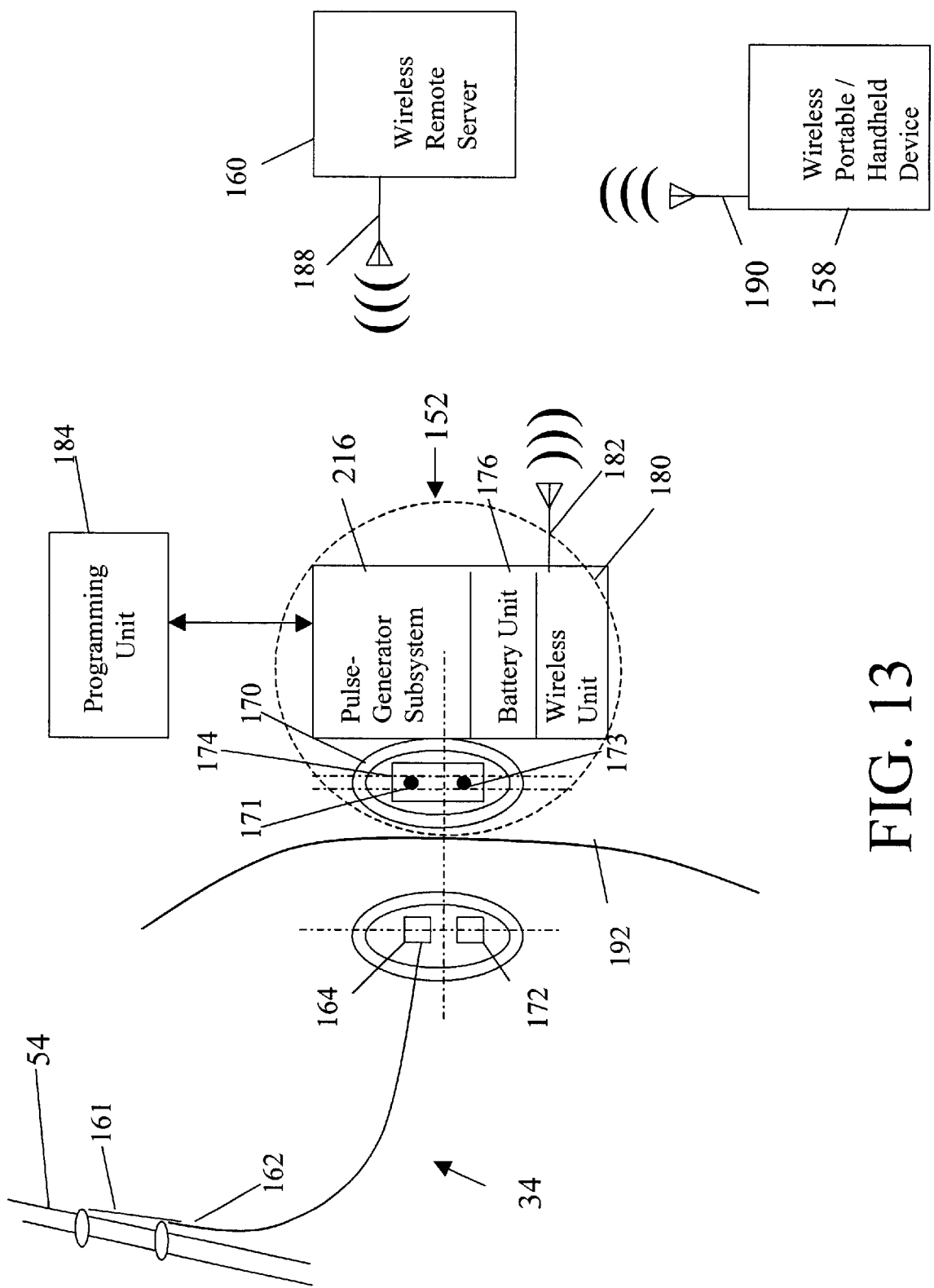
FIG. 13 shows the concept block diagram of the invention in the preferred embodiment.

The external stimulator 152 of the presently preferred embodiment, and its components are shown schematically in FIG. 13. The major components of the stimulator are the pulse generator subsystem 216, the battery unit 176, and the wireless unit (telemetry) 180. A replaceable battery 176 is used for providing power to all parts of the external stimulator circuitry. The telemetry component 180 provides wireless communication with the wireless remote server 160 using Wireless Application Protocol (WAP). The telemetry component 180 receives messages from the server 160 and supports selection of an existing program in its pre-programmed state from a library of programs. It also supports making minor variations to the parameters of an existing program for appropriate pulse signal to be generated in the external stimulator 152. A programming unit 184 can be connected by wire to the external stimulator 152 to load new predetermined programs. The external stimulator is coupled to an implanted lead-receiver 34. The implanted lead-receiver 34 has a pair of electrodes 161, 162 in contact with the nerve 54 to be stimulated, at the distal end. On the proximal end of the lead-receiver 34 is the secondary coil 168, implanted circuitry 164 and a magnet 172.

Figure 14:
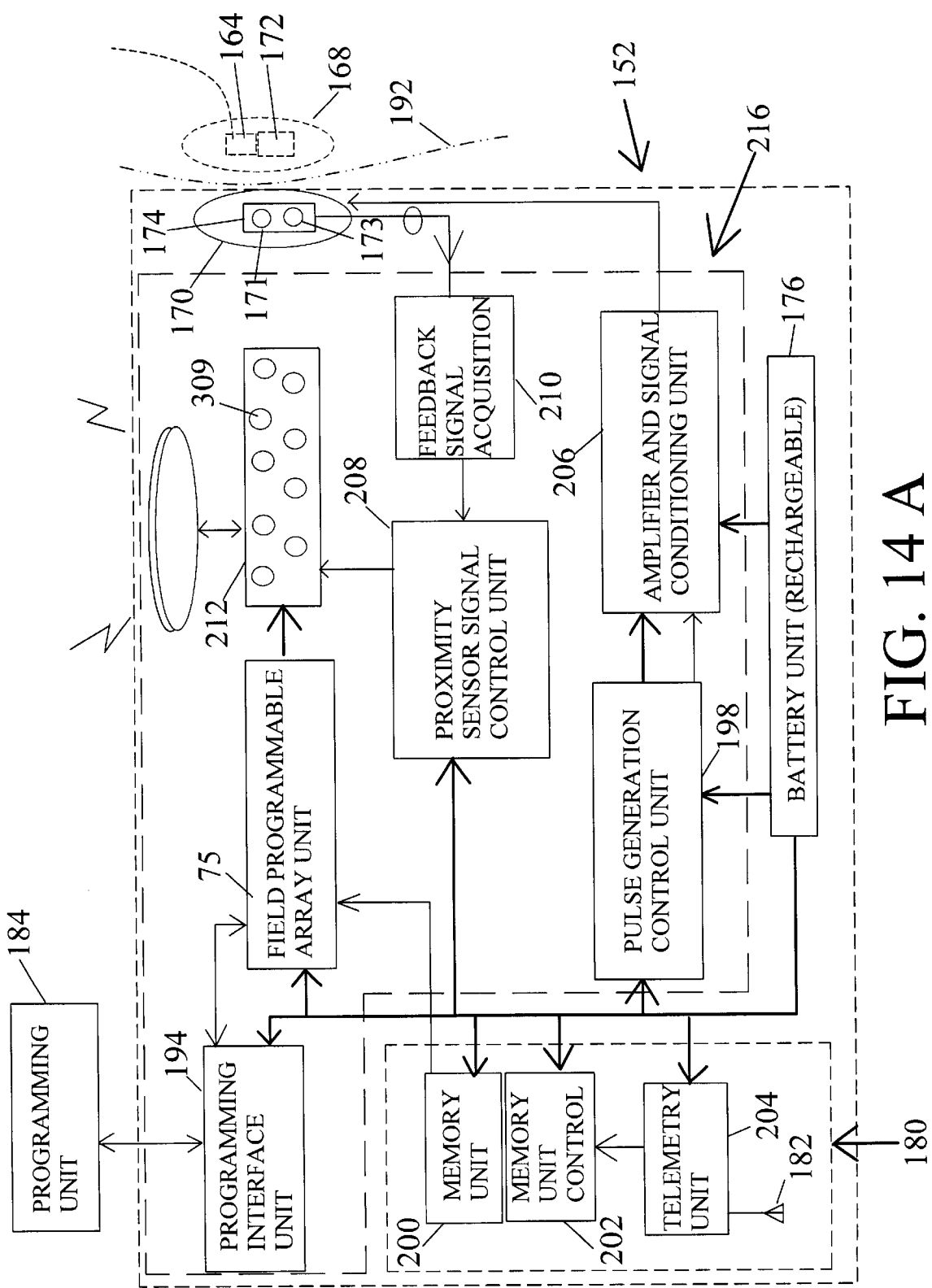
FIG. 14A is a diagram showing the primary and secondary coils separated by skin, and the components of the external stimulator.
FIG. 14B is a schematic diagram showing the programming station interfaced to the external stimulator.
Figure 14:
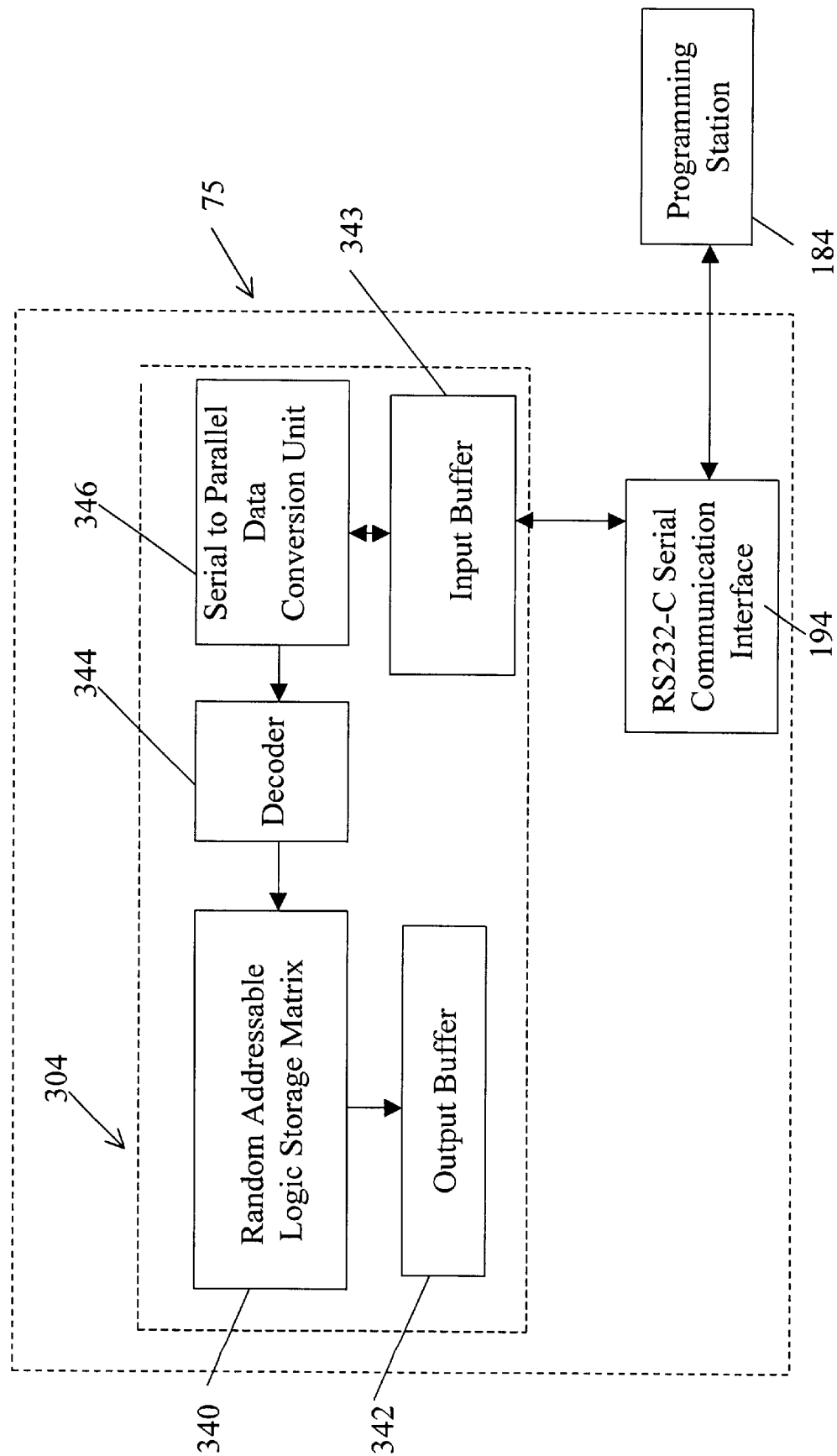

FIG. 14A shows a block diagram of the external stimulator 152. In the presently preferred embodiment, there are a limited number of predetermined programs. The programs are stored in the memory unit 200. This represents memory with a readable and writeable portion and a non-volatile pre-programmable portion, a Field Programmable Array Unit (FPGA) 75 and a random access component (RAM) 200, 202, that facilitates application of logic to edit and change the "current" parameters being utilized for pulse generation. The programmable unit interface 194 provides an interface to a programming unit (portable computer system) 184, which allows re-loading of a new set of predetermined programs. The pulse generation component 198 generates a pulse of well-defined parameters, selected from the programmed parameters that exist in the memory unit 200. The pulse signal generation unit 198 provides its signal to be amplified and conditioned at the amplifier and signal conditioning unit 206 which then provides these signals to the primary (external) inductive coil 170. A pair of sensors 174 senses the position of the implanted magnet 164 and the sensor signal is fed back to the proximity sensor control block 208 via the feedback signal conditioning unit 210. The feedback signal provides a proportional signal for modification of the frequency, amplitude and pulse-width of the pulse being generated by the pulse signal generator unit 198. In the preferred embodiment, the primary (external) coil 170 has a sensor unit 174 connected to it. The sensor unit has two sensors 171, 173 that sense the location of the implanted magnet 172.

The implanted (secondary) coil 168 is rigidly connected to the passive circuit and magnet assembly 172. The skin 192 separates the subcutaneous and supercutaneous components. The external components are patched-on to the skin, with the primary coil 170 in close proximity and optimally situated with respect to the implanted (secondary) coil 168. The external generator 152 is composed of three sub-assemblies. The first sub-assembly is the pulse generation and signal conditioning components 216, the second is the battery 176 and the third is the telemetry and memory unit 180. These modules or sub-assemblies provide for a scalable external generator box. This supports the notion of the system adapting to requirements of the application. Wireless antenna 182 provides a means of communication to the external stimulator 152 and the wireless remote server 160. The programming unit 184 can be physically connected to the stimulator 152 (via the Programming Unit Interface 194) in a tethered manner for loading of new predetermined programs or changing parameters of an existing program.

FIG. 14B shows greater details for the Programmable Logic Array Unit 75. The Input Buffer block 343 is where the serial data is stored in temporary register storage. This accumulation allows for the serial to parallel conversion to occur. The serial to 16 bit parallel block 346 sets up 16 bits of data, as created from the RS232-C serial data. This parallel data bus will communicate the data and the address information. The decoder block 344 decodes address information for the Random Addressable Logic Storage Matrix 340 from which to access the data i.e. programmer parameters. The Output Buffer 342 provides an interface to the Long Term Memory 200.

Figure 15:
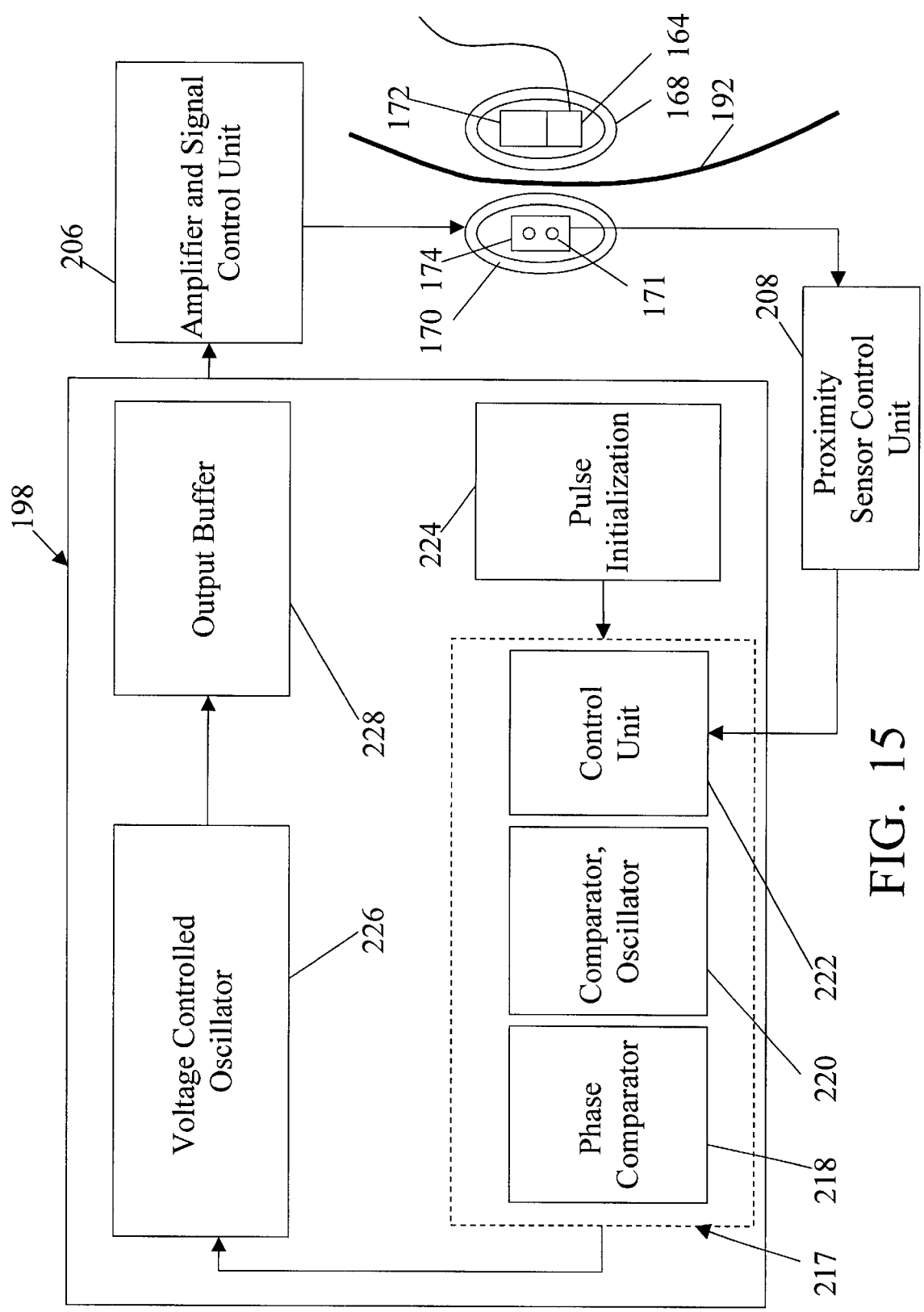
FIG. 15 shows the proximity sensing between the primary and secondary coils and feedback regulation of the pulse signals transmitted at the primary coil.

A schematic diagram of the feedback regulation of the external stimulator 152 is shown in FIG. 15. The pulse initialization block 224 provides a means to initialize the pulse signal parameters at device reset time, based on a prior selection of pulse parameters. The control unit 222 receives the appropriate signal from the proximity sensor control unit. A phase comparator 218 compares the frequency of the "expected frequency" with the "actual frequency" of the pulse. The voltage controlled oscillator (VCO) 226 receives the voltage signal from the pulse signal adapter block 217. The oscillator 226 then prepares a pulse with an appropriate pulse width, frequency and magnitude. The output buffer 228 stores the signal and also performs signal conditioning. The amplifier 206 then amplifies the signal to an appropriate level for delivery to the primary (external coil) 170. Such a method provides feedback control for the pulse signal being generated, based on the relative position of the implanted and external coils 168, 170. The magnet is rigidly connected to the implanted passive circuit 164 in the proximal end of the lead-receiver. The position of the implanted circuitry 164 and the associated magnet 172 is sensed and converted to a voltage value by the proximity sensor control unit 208.

The external stimulator 152, contains a number of predetermined (pre-packaged) programs. Some, but not all of these programs can be manually activated by the patient or caretaker (by pressing a button). Each predetermined program contains a unique combination of pulse amplitude, pulse width, frequency of pulses, on-time, and off-time. In the current embodiment, patient controlled pre-determined programs are arranged in such a way that the aggressiveness of the stimulation (therapy) increases from program #1 to program #6. Programs #7, #8, and #9 are "locked-out" to the patient or caretaker, and can be activated by the physician only.

Physician activation can be done remotely using wireless communication. The first three programs provide the least aggressive therapy, and the last three programs provide the most aggressive therapy. The following are examples of least aggressive therapy for neurological applications.

Program #1: 1.0 mAmp. current output, 0.2 milliseconds (msec.) pulse width, 15 Hz frequency, 15 sec ON time–1.0 min OFF time, in repeating cycles.

Program #2: 1.5 mAmp. current output, 0.4 msec. pulse width, 20 Hz frequency, 20 sec ON time–2.0 min OFF time, in repeating cycles.

The following are examples of more aggressive level of therapy.

Program #5: 2.0 mAmp. current output, 0.3 msec. pulse width, 25 Hz frequency, 20 sec ON time–1.0 min OFF time, in repeating cycles.

Program #6: 2.0 mAmp. current output, 0.3 msec. pulse width, 25 Hz frequency, 20 sec ON time–1.0 min OFF time, in repeating cycles.

The following are examples of physician controlled therapy.

Program #8: 3.0 mAmp. current output, 0.4 msec. pulse width, 30 Hz frequency, 40 sec ON time–1.5 min OFF time, in repeating cycles.

Program #9: 3.5 mAmp. current output, 0.5 msec. pulse width, 30 Hz frequency, 30 sec ON time–5 min OFF time, in repeating cycles.

The above programs are examples of the predetermined programs for vagus nerve stimulation (neurological applications). The actual parameter settings for any given patient may deviate somewhat from the above. As shown schematically in FIG. 13 and FIG. 14, new predetermined programs can be loaded into the external stimulator 152 with a programming unit 184 to modify the existing programs.

As in the stimulator adopted for neurological stimulation, the stimulator for urinary incontinence also contains patient controlled predetermined programs that are arranged in such a way that the aggressiveness of the stimulation (therapy) increases from program #1 to Program #6. Programs #7, #8, and #9 are "locked-out" to the patient, and can be activated by the physician only. Thus the first three programs provide the least aggressive therapy, and the last three programs provide the most aggressive therapy. The following are examples of least aggressive therapy.

Program #1: 1.5 mAmp. current output, 0.2 msec. pulse width, 10 Hz frequency.

Program #2: 2.0 mAmp. current output, 0.3 msec. pulse width, 15 Hz frequency.

The following are examples of more aggressive level of therapy.

Program #5: 2.5 mAmp. current output, 0.35 msec. pulse width, 20 Hz frequency.

Program #6: 2.5 mAmp. current output, 0.40 msec. pulse width, 30 Hz frequency.

The following are examples of physician controlled therapy.

Program #8: 3.5 mAmp. current output, 0.4 msec. pulse width, 25 Hz frequency.

Program #9: 4.5 mAmp. current output, 0.5 msec. pulse width, 30 Hz frequency.

As before, the above are examples of the predetermined programs for urinary incontinance applications. The actual parameter settings for any given patient may deviate somewhat from the above.

Figure 16:
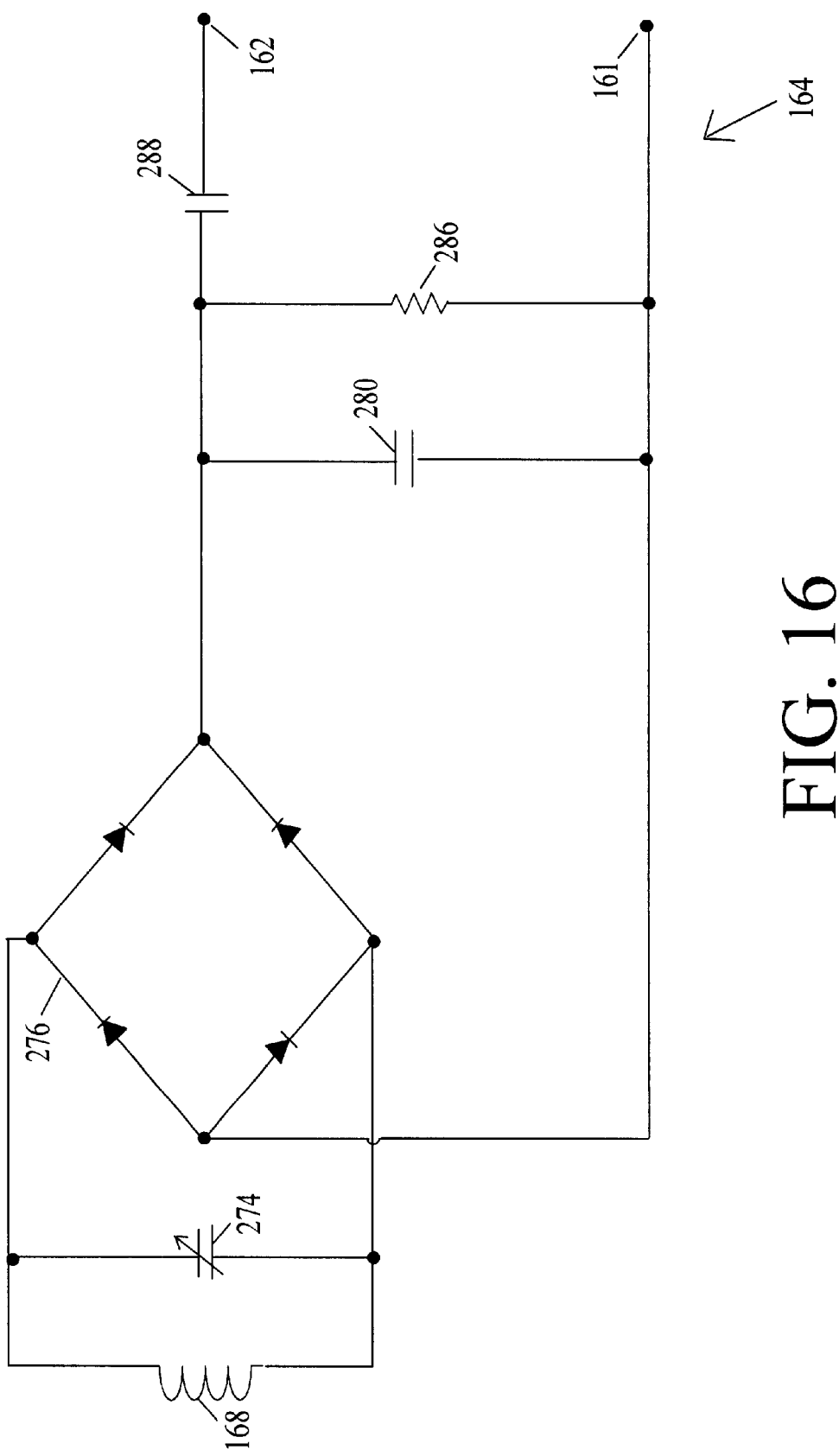
FIG. 16 shows the passive circuitry contained in the proximal end of the implantable lead-receiver.

The circuitry of the implantable lead-receiver is shown in FIG. 16. This version of the circuit uses all passive components. In the current embodiment, approximately 25 turn copper wire of 30 gauge or similar thickness is used for the primary coil 170 and secondary coil 168 element. This wire is concentrically wound with the windings all in one plane. A variable capacitor 274 provides flexibility in tuning to the actual frequency received by the subcutaneous coil 168 from the primary (external) coil 170. The frequency of the pulse-waveform delivered to subcutaneous coil element 168 can vary and so a variable capacitor 274 provides ability to tune secondary implanted circuit 172 to the signal from the primary coil 170. The diode bridge 276 rectifies the pulse signal from the implanted coil and frequency reduction is obtained by capacitor 280 and resistor 286. The last component in line is capacitor 288 which is, used for isolating the output signal from the electrode wire. The return path of signal from cathode will be through the tissue for "Bipolar" stimulation. Alternatively, the anode can be connected to the remote ground 161 connection of implantable circuit, providing for much larger intermediate tissue for "Unipolar" stimulation. The "Bipolar" stimulation offers localized stimulation of tissue compared to "Unipolar" stimulation, where skeletal muscles can be stimulated. For this reason, the presently preferred embodiment is configured for "Bipolar" stimulation. The implanted circuit in this embodiment is passive, so a battery does not have to be implanted. It is however possible, in a future version, with appropriate modifications, to implant a battery source for use of active component logic in the implant.

Figure 17:
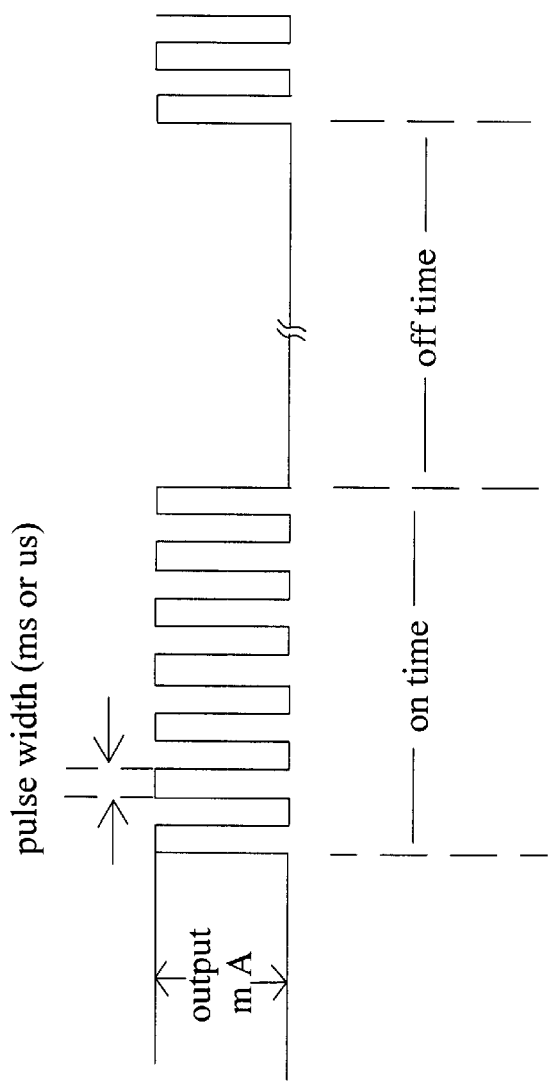
FIG. 17 is a diagram showing the morphology of the output pulses
Figure 18:
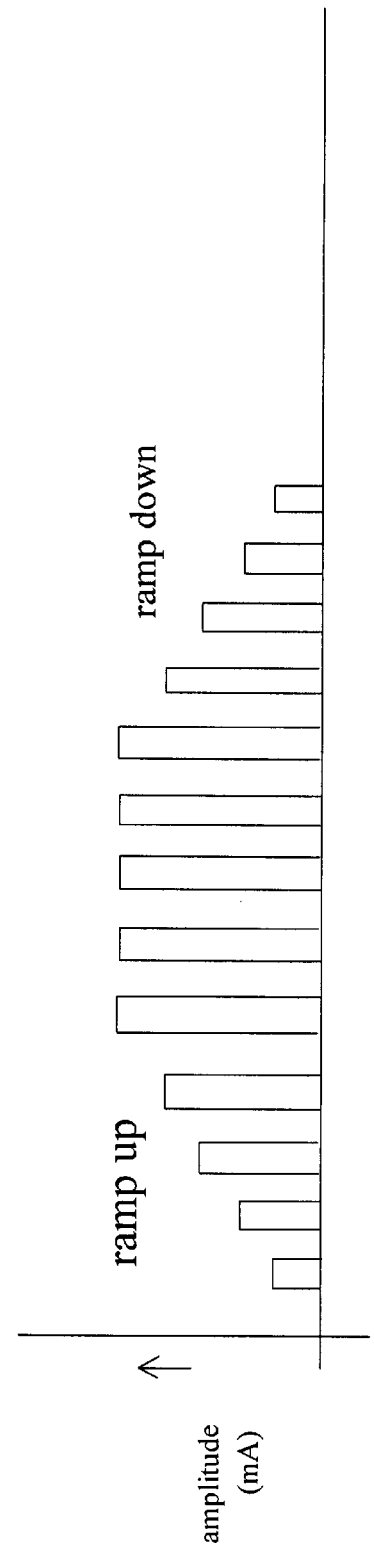
FIG. 18 shows the ramping up and ramping down of the stimulation pulses.

The morphology of the pulse signals is shown in FIG. 17, and FIG. 18 shows the ramp-up and ramp-down functionality of the pulse signals generated for patient comfort.

Figure 19:
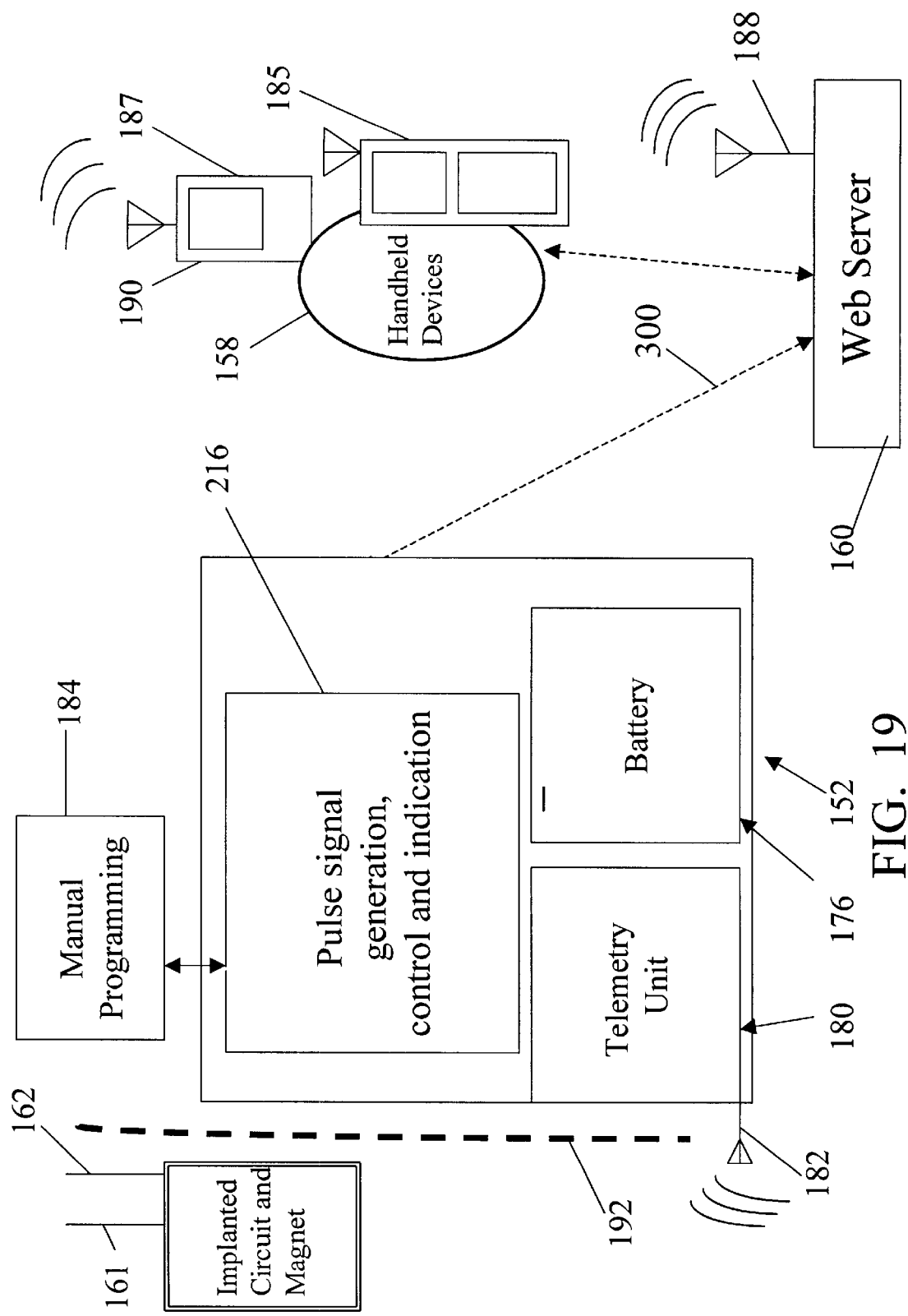
FIG. 19 shows the flow of data between a physician's handheld device and the external stimulator via a server, using the web application protocol.

FIG. 19 shows schematically the communication between the pulse generator 152 and the remote hand-held computer. A desktop or laptop computer can be a server 160 which is situated remotely, perhaps at a health-care provider's facility or a hospital. The data can be viewed at this facility or reviewed remotely by medical personnel on a hand-held personal data assistant (PDA) 158, such as a "palm-pilot" from PALM corp. (Santa Clara, Calif.), a "Visor" from Handspring Corp. (Mountain view, Calif.) or on a personal computer (PC) available from numerous vendors. The physician or appropriate medical personnel, is able to interrogate the external stimulator 152 device and know what the device is currently programmed to, as well as, get a graphical display of the pulse train. The wireless communication with the remote server 160 and hand-held PDA 158 can be supported in all geographical locations within and outside the United States (US) that provides cell phone voice and data communication service. The pulse generation parameter data can also be viewed on the handheld devices (PDA) 158.

The telecommunications component of this invention uses Wireless Application Protocol (WAP). The Wireless Application Protocol (WAP) is a set of communication protocols standardizing Internet access for wireless devices. Previously, manufacturers used different technologies to get Internet on hand-held devices. With WAP, devices and services interoperate. WAP promotes convergence of wireless data and the Internet. The WAP Layers are Wireless Application Envirnment (WAEW), Wireless Session Layer (WSL), Wireless Transport Layer Security (WTLS) and Wireless Transport Layer (WTP).

Figure 20:
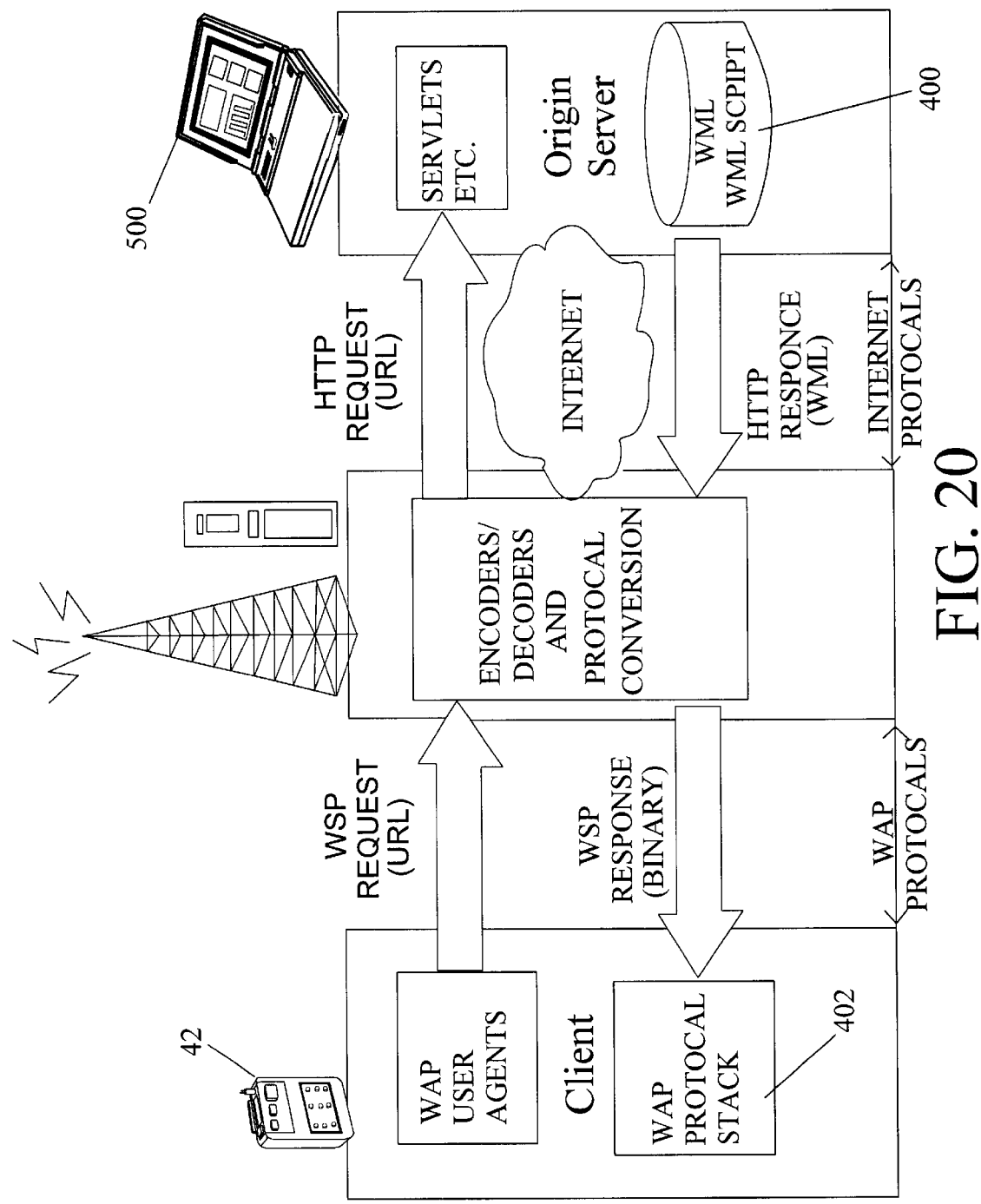
FIG. 20 is a schematic flow diagram of wireless application protocol.

The WAP programming model is heavily based on the existing Internet programming model, and is shown schematically in FIG. 20. Introducing a gateway function provides a mechanism for optimizing and extending this model to match the characteristics of the wireless environment. Over-the-air traffic is minimized by binary encoding/decoding of Web pages and readapting the Internet Protocol stack to accommodate the unique characteristics of a wireless medium such as call drops. Such features are facilitated with WAP The key components of the WAP technology, as shown in FIG. 20, includes 1) Wireless Mark-up Language (WML) 400 which incorporates the concept of cards and decks, where a card is a single unit of interaction with the user. A service constitutes a number of cards collected in a deck. A card can be displayed on a small screen. WML supported Web pages reside on traditional Web servers. 2) WML Script which is a scripting language, enables application modules or applets to be dynamically transmitted to the client device and allows the user interaction with these applets. 3) Microbrowser, which is a lightweight application resident on the wireless terminal that controls the user interface and interprets the WML/WMLScript content. 4) A lightweight protocol stack 402 which minimizes bandwidth requirements, guaranteeing that a broad range of wireless networks can run WAP applications. The protocol stack of WAP can comprise a set of protocols for the transport (WTP), session (WSP), and security (WTLS) layers. WSP is binary encoded and able to support header caching, thereby economizing on bandwidth requirements. WSP also compensates for high latency by allowing requests and responses to be handles asynchronously, sending before receiving the response to an earlier request. For lost data segments, perhaps due to fading or lack of coverage, WTP only retransmits lost segments using selective retransmission, thereby compensating for a less stable connection in wireless. The above mentioned features are industry standards adopted for wireless applications and greater details have been publicized , and well knownn to those skilled in the art.

The presently preferred embodiment utilizes WAP, because WAP has the following advantages, 1) WAP protocol uses less than one-half the number of packets that the standard HTTP or TCP/IP Internet stack uses to deliver the same content. 2) Addressing the limited resources of the terminal, the browser, and the lightweight protocol stack are designed to make small claims on CPU and ROM. 3) Binary encoding of WML and SMLScript helps keep the RAM as small as possible. And, 4) Keeping the bearer utilization low takes account of the limited battery power of the terminal.

In this embodiment two modes of communication are possible. In the first, the server initiates an upload of the actual parameters being applied to the patient, receives these from the stimulator, and stores these in its memory, accessible to the authorized user as a dedicated content driven web page. The web page is managed with adequate security and password protection. The physician or authorized user can make alterations to the actual parameters, as available on the server, and then initiate a communication session with the stimulator device to download these parameters.

The physician is also able to set up long-term schedules of stimulation therapy for their patient population, through wireless communication with the server. The server in turn communicates these programs to the neurostimulator. For instance, a physician may program an Alzheimer's patient to a stimulation program for two weeks, and program an epilepsy patient to a selected long-term "on", "off" stimulation therapy. Each schedule is securely maintained on the server, and is editable by the physician and can get uploaded to the patient's stimulator device at a scheduled time. Thus, therapy can be customized for each individual patient. Each device issued to a patient has a unique identification key in order to guarantee secure communication between the wireless server 160 and stimulator device 152.

Figure 21:
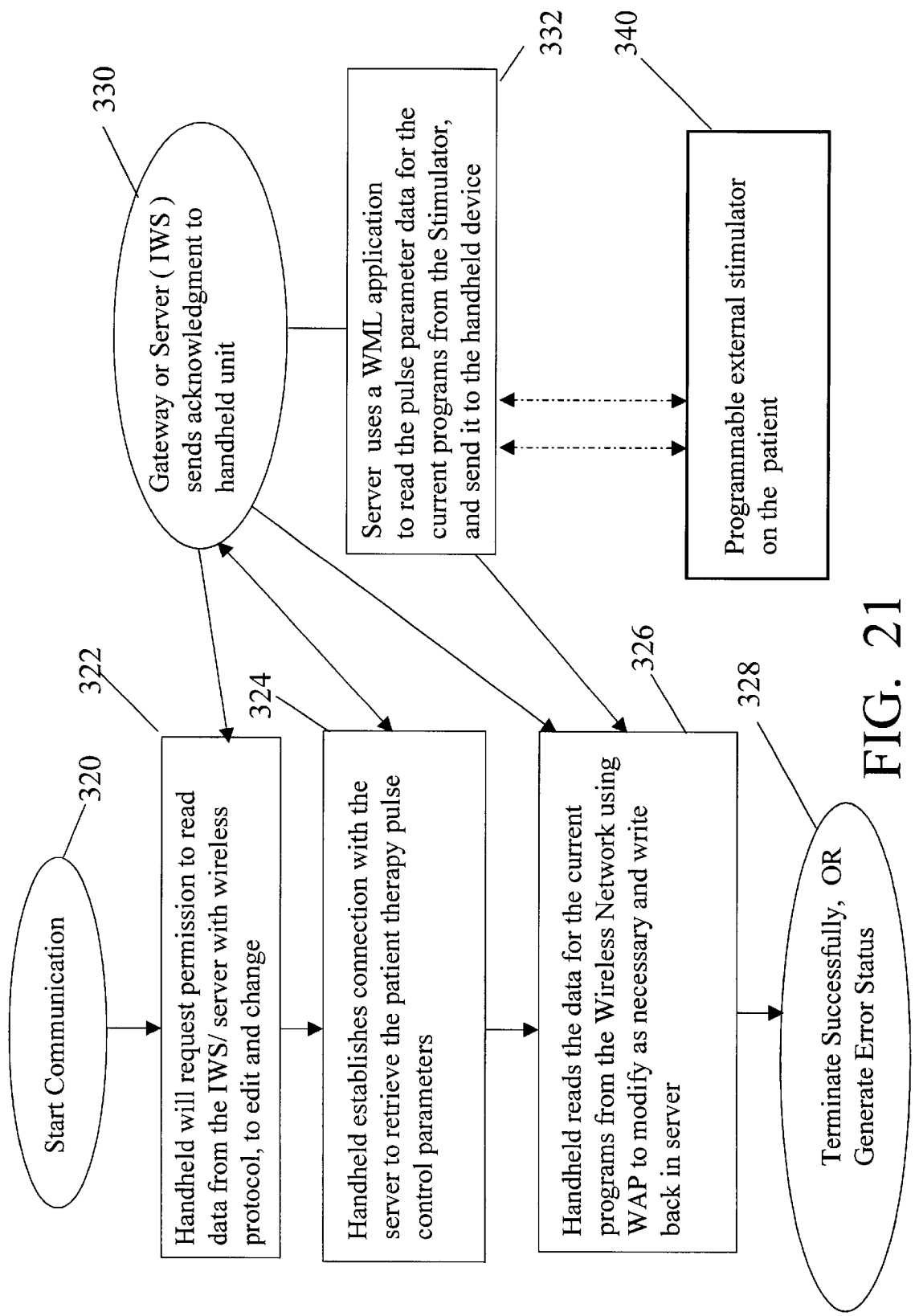
FIG. 21 is a flowchart showing the algorithm for wireless communication between the physician's handheld device and the long-term storage at a server.
Figure 22:
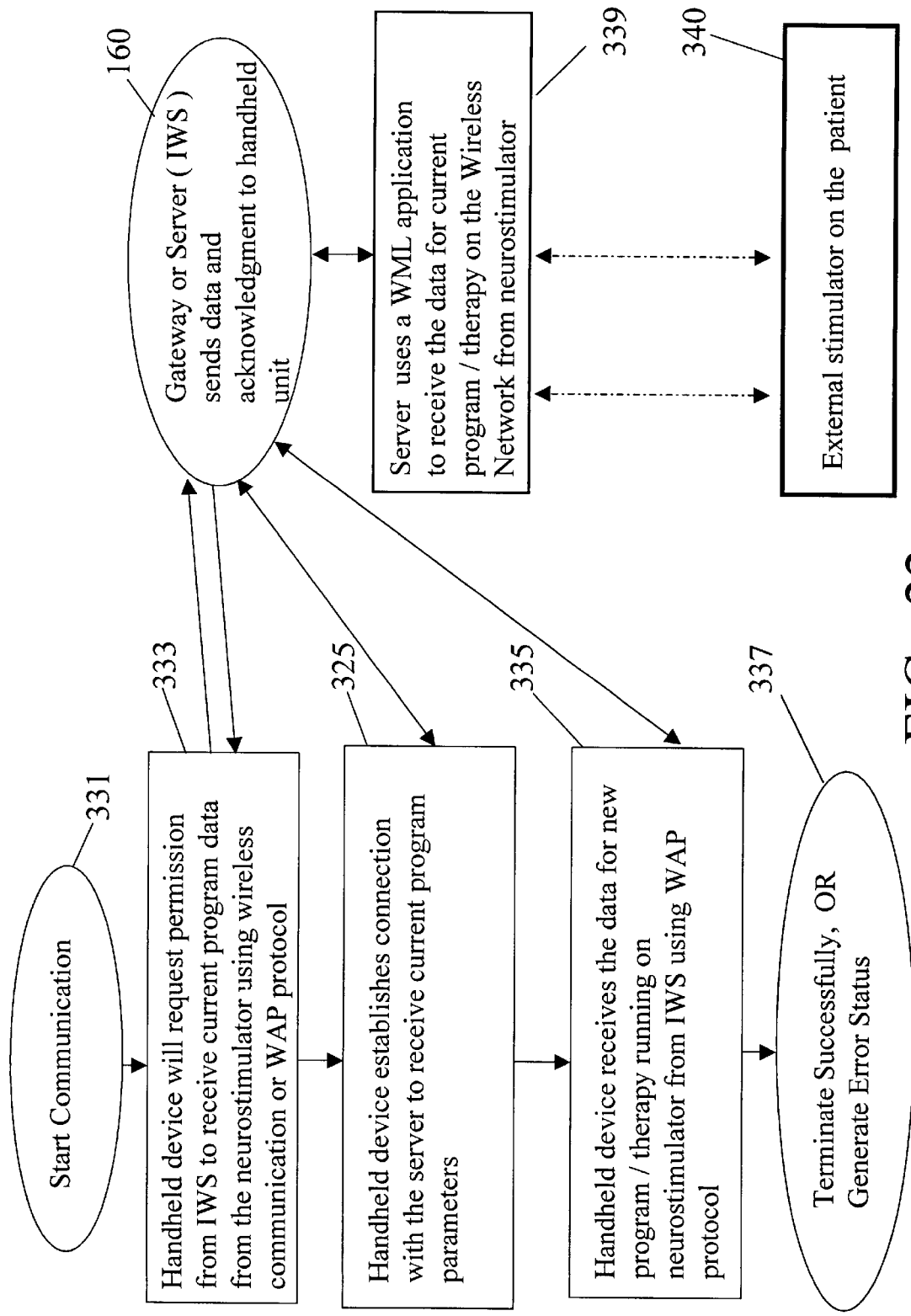
FIG. 22 is a flowchart showing the algorithm of wireless communication between the physician's handheld device and the external stimulator.

The second mode of communication is the ability to remotely interrogate and monitor the stimulation therapy on the physician's handheld (PDA) 158. The algorithms for remote wireless communication are shown in FIGS. 21 and 22. In FIG. 21 the hand-held device initiates communication with the server (IWS) 160 using the steps in methods 322. The server (IWS) 160 sends acknowledgment 330 back to the hand-held indicating a successful communication link. The program-selection data can be pre-loaded in the handheld or loaded on request from the database on the IWS 160, and the IWS 160 and handheld communicate for this purpose. The IWS 160 sends acknowledgment on successful communication of data stream to the handheld. The purpose of this algorithm is to provide a scheme for communication between the handheld and the IWS 160. This scheme provides for the program parameters, resident at the IWS 160, to be uploaded to the hand-held. The parameter and patient history information changes get made at the handheld and these changes are downloaded back to the IWS 160. The IWS 160 performs some error checking at this point to verify that the selection and changes are feasible. A patient database is maintained at the IWS 160 and it is updated as patients are inserted there 326. The IWS 160 then sends the program parameters to the external stimulator 152 based on a different algorithm. A successful termination of a communication session between the handheld and IWS 160 is made after all relevant data is communicated 328.

FIG. 22 shows the ability of the wireless network to retrieve parameters from the external stimulator 152 which is physically patched on the patient. This algorithm supports the communication between the pulse generator 152 and the IWS 160. The IWS 160 can read from the pulse generator 152. This includes a request for data, sent to the IWS 160 from handheld 333, and then a request is sent to the pulse generator 152 from IWS 160, followed by pulse generator 152 sending the parameters for the current program back to the IWS 160. The parameters utilized for the current therapy cycle, can be queried by the server (IWS) 160 with wireless communication provided by WAP based algorithms. These parameters can then be communicated to the handheld device, shown as steps 325, 335. The hand held can either select a new program, (which comes with its own set of parameters) or allows user to edit the existing parameters of a pre-loaded program with changes within some small bounds. This step is not shown in the algorithm, but is implied as an intuitive extension. These changes are communicated to the IWS 160 with method 335 and then the data provided back to the handheld.

The algorithms on the IWS 160 checks for the validity of the modified parameters prior to downloading them to the programmable stimulator attached on the patient 340 for a new version of the program. Since it is important to verify the validity of the parameters used for pulse generation, it is done at two levels. The first and most important level of checking is done at the IWS 160. Any change being made to the parameters by the handheld user, has to be verified prior to being committed in the patient database. The second level of error checking is done when the parameters at the external stimulator 152 are queried by the IWS 160 and these parameters should match the values in the IWS 160 database for the particular patient.

Figure 23:
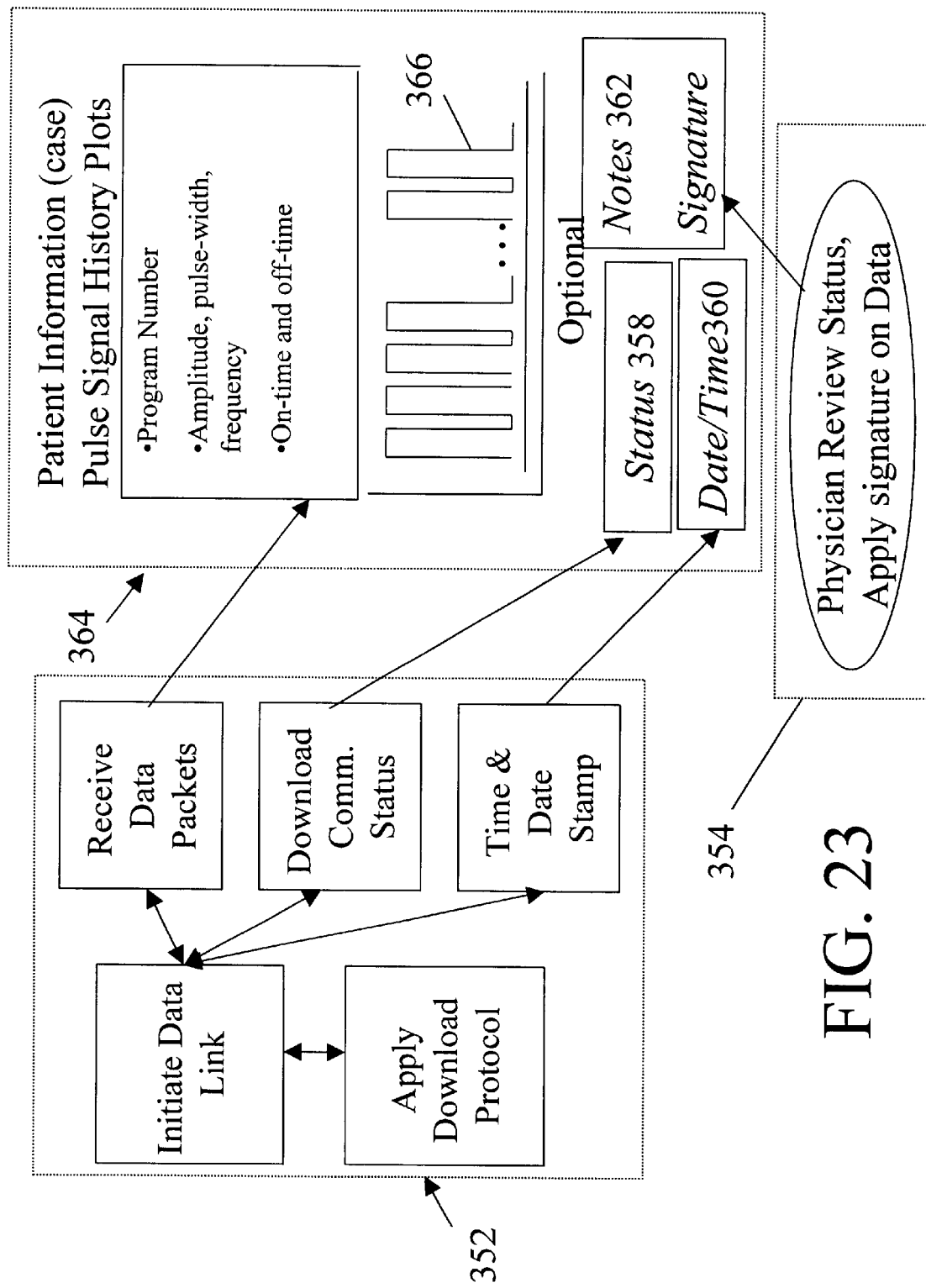
FIG. 23 is a diagram which shows the information available on a web-page at the server.

FIG. 23 shows visualization process of the data received from the hand-held device (PDA) 158 and the external stimulator 152 to the IWS 160. This data is then available at the IWS 160 and accessed by running a web-server. The web pages 364 at the server provide ability of the health care provider, with proper authorization, to select new prepackaged pulse generation programs or edit existing ones. The parameters of an existing program can be edited, and a schedule can be prepared for application to the pulse generator of a particular patient. The parameters such as, program number, amplitude, pulse-width and frequency etc. are maintained and modified. A graphical plot of the pulse signal can also be visualized as an optional plot 366. The appropriate individual, such as the physician, can review the above information 364 and examine status 358, 360 make changes, apply notes and his/her signature 362 to the patient record. Some portion of this information can also be downloaded to the physician's hand-held device for review and changes. This information will be limited to patient history, the program being utilized and parameters being used for the program 364. This communication is encrypted.

In another embodiment of this invention, infrared communication can be used for communication between the hand-held programmable unit 184 and the programmer unit interface 194. This requires, preferably, a line of sight between the two. The inexpensive and widely available short-range infrared transceivers are used at the communication points. These adhere to the Infrared Data Association (IrDA) standards. This standard also allows communication between Microsoft's Windows operating system devices and other non-Windows based devices, as an example. Both a "walk-up" and a "point to point" model is supported.

It will be apparent to one skilled in the art, that the same methodology of telemetric communication can be adapted or added to the physical packaging of the apparatus shown in FIG. 12. In such a case, a separate module containing the applicable components of the wireless telemetry unit, on one or more boards will be plugged into or added to the stimulator package. Once adopted to the packaging of such a stimulator, the methodology of wireless communication between the external stimulator and IWS and physician, described in this application applies in its entirety. It is therefore desired that the present embodiment be considered in all aspects as illustrative and not restrictive, reference being made to the appended claims rather than to the foregoing description to indicate the scope of the invention.

What is claimed is:

1. A method for at least one of activating, de-activating, or interrogating pre-packaged programs of a neuro-stimulator system, through a remote server using the internet, comprising the steps of:
    a) providing a neuro-stimulator system; said neuro-stimulator system comprising an implanted stimulus-receiver and an external stimulator with wireless telemetry means;
    b) providing said external stimulator with at least two pre-packaged therapy programs, said programs comprising pre-determined combinations of stimulation parameters for electrical pulses;
    c) deciding said pre-packaged program needs to be altered remotely;
    d) connecting said external stimulator wirelessly with a remote server using the internet; and
    e) communicating bi-directionally between said server and said external stimulator to exchange data for at least one of activation, de-activation or interrogation of said pre-packaged therapy programs.

2. A method of claim 1, wherein said external stimulator further comprises a means for locking out one of said pre-packaged therapy programs to the patient.

3. The method of claim 1, wherein said external stimulator comprises means for inductively coupling with an implanted stimulus receiver, for providing therapy to a patient.

4. A method for at least one of remotely controlling, interrogating a neuro-stimulator with a hand-held computer unit through a remote server, comprising the steps of:
    a) providing a neuro-stimulator systems said neuro-stimulator system comprising implanted components and an external stimulator;
    b) providing said external stimulator with wireless telemetry means, said stimulator comprising pre-determined programs which define parameters of electrical pulses;
    c) deciding to change programs of external stimulator remotely;
    c) connecting wirelessly said external stimulator with said remote server; and
    d) providing means for wireless, bi-directional communication between said remote server and said external stimulator to exchange data, said server also exchanging data wirelessly with said hand-held computer unit, whereby said programs are remotely controlled and interrogated.

5. The method of claim 4, wherein said external stimulator is inductively coupled to an implanted stimulus receiver, for providing therapy.

6. The method of claim 4, wherein said external stimulator further compromises means to modify said at least two pre-determined therapy programs.

7. The method of claim 4, wherein said remote control is executed from the server at pre-determined time intervals.

8. A method of claim 4, wherein said external tissue stimulator further comprises means for locking out one of said pre-determined therapy programs to the patient.

9. A method for at least one of remotely controlling, interrogating the therapy programs of a neuro-stimulator with a handheld computer unit using internet server, comprising the steps of:
    a) providing a neuro-stimulator system; said neuro-stimulator system comprising an implanted stimulus-receiver and an external stimulator with wireless telemetry means;
    b) providing said external stimulator with therapy programs, said therapy programs comprising pre-determined combinations of stimulation parameters of electrical pulses;
    c) communicating bi-directionally, wirelessly, between said external stimulator and said internet server; and
    d) communicating bi-directionally between said handheld computer unit and said server using Wireless Application Protocol (WAP) to remotely operate said therapy programs,
    whereby said therapy programs are remotely controlled and interrogated.

10. The method of claim 9, wherein the parameter values of said programs are verified remotely, using said server.

11. The method of claim 9, wherein the up-link of program data from the server is done at a pre-determined time intervals, for transmission at a later date.

12. The method of claim 9 wherein, remote control comprises remote activation and deactivation of said therapy programs.

13. A neuro-stimulation system to provide therapy for neurological disorders comprising means for at least one of remotely controlling, interrogating the therapy programs with a hand-held computer unit through a remote server, comprising:
    a) said neuro-stimulation system comprising an implanted stimulus-receiver and an external stimulator;
    b) said external stimulator comprising means for wireless telemetry, and at least two pre-packaged therapy programs which define parameters of electrical pulses;
    c) means for wirelessly connecting said external stimulator with said remote server; and
    d) means for wireless, bi-directional communication between said remote server and said external stimulator to exchange data, said server also exchanging data wirelessly with said hand-held computer unit,
    whereby said therapy programs are remotely controlled and interrogated.

14. The system of claim 13, wherein said external stimulator is inductively coupled with an implanted stimulus-receiver, for providing neuromodulation therapy.

15. The sysem of claim 13 wherein, said remote control comprises remote activation and deactivation of said therapy programs.

16. The system of claim 13 wherein, said remote control comprises remote alteration of said therapy programs which define electrical stimulation parameters.

17. The system of claim 13, wherein said external tissue stimulator further comprises means for modifying said therapy programs.

18. The system of claim 13, wherein said external stimulator further comprises means to lock out at least one of said therapy program to the patient.

19. A neuro-stimulation system comprising means for at least one of remotely controlling, interrogating the therapy programs of an external tissue stimulator with a hand-held computer unit through a remote server using the internet, comprising:
- a) said neuro-stimulation system comprising an implanted stimulus-receiver and an external tissue stimulator;
- b) said external tissue stimulator having means for wireless telemetry, said stimulator comprising at least two said therapy programs which define parameters of electrical pulses;
- c) means for communicating bi-directionally, wirelessly, between said external tissue stimulator and said remote server.
- d) means for communicating bi-directionally between said handheld computer unit and said server using Wireless Application Protocol (WAP) to remotely operate said therapy programs,
  - whereby said external stimulator is remotely controlled and interrogated.

20. The system of claim 19, wherein said external tissue stimulator is inductively coupled with an implanted stimulus-receiver, for providing therapy.

21. The system of claim 19, wherein the current status of said programs for said electrical stimulator is verified remotely, using said server.

22. The system of claim 19, wherein schedules for stimulation therapy may be set up and executed on said server.

23. The system of claim 19, wherein the up-link of program data from said server is done at a scheduled time intervals.

24. The system of claim 19 wherein, remote control comprises at least one of remote activation, and deactivation of said therapy programs.

* * * * *